United States Patent
Uemori et al.

(10) Patent No.: US 12,359,177 B2
(45) Date of Patent: Jul. 15, 2025

(54) DNA POLYMERASE MUTANT SUITED TO NUCLEIC ACID AMPLIFICATION FROM RNA

(71) Applicant: TAKARA BIO INC., Shiga (JP)

(72) Inventors: Takashi Uemori, Otsu (JP); Hiroyuki Matsumoto, Santa Clara, CA (US); Kensuke Saito, Kusatsu (JP); Miwa Akitomo, Kyoto (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 18/660,667

(22) Filed: May 10, 2024

(65) Prior Publication Data

US 2024/0309341 A1    Sep. 19, 2024

Related U.S. Application Data

(62) Division of application No. 17/257,986, filed as application No. PCT/JP2019/026513 on Jul. 3, 2019, now Pat. No. 12,018,294.

(30) Foreign Application Priority Data

Jul. 13, 2018    (JP) ................................ 2018-133086

(51) Int. Cl.
*C12N 9/12*    (2006.01)
(52) U.S. Cl.
CPC .... *C12N 9/1252* (2013.01); *C12Y 207/07007* (2013.01)
(58) Field of Classification Search
None
See application file for complete search history.

(56) References Cited

U.S. PATENT DOCUMENTS

| | | | |
|---|---|---|---|
| 5,830,714 | A | 11/1998 | Swaminathan et al. |
| 7,179,590 | B2 | 2/2007 | Smith |
| 8,759,061 | B1 | 6/2014 | Marx et al. |
| 2002/0012970 | A1 | 1/2002 | Smith et al. |
| 2003/0044817 | A1 | 3/2003 | Laird et al. |
| 2010/0221787 | A1 | 9/2010 | Hayashizaki et al. |
| 2013/0034879 | A1 | 2/2013 | Skirgaila et al. |
| 2013/0149748 | A1 | 6/2013 | Bauer et al. |
| 2014/0051126 | A1 | 2/2014 | Bauer et al. |
| 2014/0170730 | A1 | 6/2014 | Suko |
| 2015/0184226 | A1 | 7/2015 | Bauer et al. |
| 2017/0029792 | A1 | 2/2017 | Bauer et al. |
| 2017/0081646 | A1 | 3/2017 | Skirgaila et al. |
| 2018/0135033 | A1 | 5/2018 | Bauer et al. |
| 2018/0346889 | A1 | 12/2018 | Ishino et al. |
| 2019/0055527 | A1 | 2/2019 | Ishino et al. |

FOREIGN PATENT DOCUMENTS

| | | |
|---|---|---|
| EP | 1 152 062 | 11/2001 |
| EP | 1 201 768 | 5/2002 |
| EP | 2 554 665 | 2/2013 |
| JP | 2000-508538 | 7/2000 |
| JP | 3844975 | 9/2002 |
| JP | 2007-520227 | 7/2007 |
| JP | 2017-178804 | 10/2017 |
| JP | 2019-162106 | 9/2019 |
| WO | 2007/143436 | 12/2007 |
| WO | 2009/054510 | 4/2009 |
| WO | 2012/139748 | 10/2012 |
| WO | 2013/083264 | 6/2013 |
| WO | 2014/090836 | 6/2014 |
| WO | 2017/090684 | 6/2017 |
| WO | 2017/090685 | 6/2017 |

OTHER PUBLICATIONS

Franceus et al., J. Ind. Microbiol. Biotechnol. vol. 44, pp. 687-695, 2017.*
See Ngo et al. in The Protein Folding Problem and Tertiary Structure Prediction, 1994, Merz et al. (ed.), Birkhauser, Boston, MA, pp. 433 and 492-495.*
Aye et al., "Engineering of DNA polymerase I from *Thermus thermophilus* using compartmentalized self-replication", Biochemical and Biophysical Research Communications, 499(9): 170-176 (2018).
Loh et al., "Mutability of DNA polymerase I: Implications for the creation of mutant DNA polymerases", DNA Repair, 4(12): 1390-1398 (2005).
Simon et al., "Rapid Identification of Genes Encoding DNA Polymerases by Function-Based Screening of Metagenomic Libraries Derived from Glacial Ice", Applied and Environmental Microbiology, 75(9): 2964-2968 (2009).

(Continued)

*Primary Examiner* — Richard G Hutson
(74) *Attorney, Agent, or Firm* — Wenderoth, Lind & Ponack, L.L.P.

(57) ABSTRACT

Provided are: a DNA polymerase mutant having reverse transcriptase activity, the DNA polymerase mutant including a sequence consisting of twelve specific amino acids A1-A12, wherein the DNA polymerase mutant having reverse transcriptase activity is characterized in that the A3 and/or A10 amino acid is substituted by a basic amino acid residue different from that prior to the introduction of mutation; a kit and a composition including the DNA polymerase; a method for producing the DNA polymerase; and a method for modifying an existing DNA polymerase having reverse transcriptase activity.

5 Claims, No Drawings
Specification includes a Sequence Listing.

(56) References Cited

OTHER PUBLICATIONS

International Preliminary Report on Patentability, issued Jan. 19, 2021 in corresponding International Patent Application No. PCT/JP2019/026513.
International Search Report, issued Oct. 1, 2019 in corresponding International Patent Application No. PCT/JP2019/026513.
Office Action issued Jun. 16, 2023 in corresponding European Patent Application No. 19833322.1.
Office Action with the Search Report issued Aug. 23, 2023 in corresponding Chinese Patent Application No. 201980046835.1, with English-language translation.
Uniprot Accession No. P52028, Jan. 31, 2018.
Office Action issued May 9, 2023 in corresponding Japanese Patent Application No. 2020-530136, with English translation, 6 pages.
Communication pursuant to Article 94(3) EPC issued Dec. 1, 2022 in European Patent Application No. 19 833 322.1.
Extended European Search Report issued Mar. 4, 2022 in European Patent Application No. 19833322.1.

* cited by examiner

```
                          SEQUENCE LISTING

Sequence total quantity: 28
SEQ ID NO: 1            moltype = AA  length = 834
FEATURE                 Location/Qualifiers
source                  1..834
                        mol_type = protein
                        organism = Thermus thermophilus
SEQUENCE: 1
MEAMLPLFEP KGRVLLVDGH HLAYRTFFAL KGLTTSRGEP VQAVYGFAKS LLKALKEDGY   60
KAVFVVFDAK APSFRHEAYE AYKAGRAPTP EDFPRQLALI KELVDLLGFT RLEVPGYEAD  120
DVLATLAKKA EKEGYEVRIL TADRDLYQLV SDRVAVLHPE GHLITPEWLW EKYGLRPEQW  180
VDFRALVGDP SDNLPGVKGI GEKTALKLLK EWGSLENLLK NLDRVKPENV REKIKAHLED  240
LRLSLELSRV RTDLPLEVDL AQGREPDREG LRAFLERLEF GSLLHEFGLL EAPAPLEEAP  300
WPPPEGAFVG FVLSRPEPMW AELKALAACR DGRVHRAADP LAGLKDLKEV RGLLAKDLAV  360
LASREGLDLV PGDDPMLLAY LLDPSNTTPE GVARRYGGEW TEDAAHRALL SERLHRNLLK  420
RLEGEEKLLW LYHEVEKPLS RVLAHMEATG VRLDVAYLQA LSLELAEEIR RLEEEVFRLA  480
GHPFNLNSRD QLERVLFDEL RLPALGKTQK TGKRSTSAAV LEALREAHPI VEKILQHREL  540
TKLKNTYVDP LPSLVHPRTG RLHTRFNQTA TATGRLSSSD PNLQNIPVRT PLGQRIRRAF  600
VAEAGWALVA LDYSQIELRV LAHLSGDENL IRVFQEGKDI HTQTASWMFG VPPEAVDPLM  660
RRAAKTVNFG VLYGMSAHRL SQELAIPYEE AVAFIERYFQ SFPKVRAWIE KTLEEGRKRG  720
YVETLFGRRR YVPDLNARVK SVREAAERMA FNMPVQGTAA DLMKLAMVKL FPRLREMGAR  780
MLLQVHDELL LEAPQARAEE VAALAKEAME KAYPLAVPLE VEVGMGEDWL SAKG        834

SEQ ID NO: 2            moltype = DNA  length = 23
FEATURE                 Location/Qualifiers
misc_feature            1..23
                        note = PCR forward Primer lambda RNA
source                  1..23
                        mol_type = other DNA
                        organism = synthetic construct
SEQUENCE: 2
caggtggcgt attccagatt gtc                                           23

SEQ ID NO: 3            moltype = DNA  length = 20
FEATURE                 Location/Qualifiers
misc_feature            1..20
                        note = PCR Reverse Primer lambda RNA
source                  1..20
                        mol_type = other DNA
```

```
                        organism = synthetic construct
SEQUENCE: 3
gcaccatact ggcaccgaga                                                    20

SEQ ID NO: 4           moltype = DNA  length = 18
FEATURE                Location/Qualifiers
misc_feature           1..18
                       note = Probe lambda RNA. 5'-end is labeled FAM and 3'-end
                        is labeled BHQ1
source                 1..18
                       mol_type = other DNA
                       organism = synthetic construct
SEQUENCE: 4
accaccggcc ccaatggc                                                      18

SEQ ID NO: 5           moltype = AA  length = 834
FEATURE                Location/Qualifiers
REGION                 1..834
                       note = DNA polymerase variant Tth b13
source                 1..834
                       mol_type = protein
                       organism = synthetic construct
SEQUENCE: 5
MEAMLPLFEP KGRVLLVDGH HLAYRTFFAL KGLTTSRGEP VQAVYGFAKS LLKALKEDGY    60
KAVFVVFDAK APSFRHEAYE AYKAGRAPTP EDFPRQLALI KELVDLLGFT RLEVPGYEAD   120
DVLATLAKKA EKEGYEVRIL TADRDLYQLV SDRVAVLHPE GHLITPEWLW EKYGLRPEQW   180
VDFRALVGDP SDNLPGVKGI GEKTALKLLK EWGSLENLLK NLDRVKPENV REKIKAHLED   240
LRLSLELSRV RTDLPLEVDL AQGREPDREG LRAFLERLEF GSLLHEFGLL EAPAPLEEAP   300
WPPPEGAFVG FVLSRPEPMW AELKALAACR DGRVHRAADP LAGLKDLKEV RGLLAKDLAV   360
LASREGLDLV PGDDPMLLAY LLDPSNTTPE GVARRYGGEW TEDAAHRALL SERLHRNLLK   420
RLEGEEKLLW LYHEVEKPLS RVLAHMEATG VRLDVAYLQA LSLELAEEIR RLEEEVFRLA   480
GHPFNLNSRD QLERVLFDEL RLPALGKTQK TGKRSTSAAV LEALREAHPI VEKILQHREL   540
TKLKNTYVDP LPSLVHPRTG RLHTRFNQTA TATGRLSSSD PNLQNIPVRT PLGQRIRRAF   600
VAEAGWALVA LDYSQIELRV LAHLSGDENL IRVFQEGKDI HTQTASWMFG VPPEAVDPLM   660
RRAAKTVNFG VLYGMSAHRL SRELAIPYEE AVAFIERYFQ SFPKVRAWIE KTLEEGRKRG   720
YVETLFGRRR YVPDLNARVK SVREAAERMA FNMPVQGTAA DLMKLAMVKL FPRLREMGAR   780
MLLQVHDELL LEAPQARAEE VAALAKEAME KAYPLAVPLE VEVGMGEDWL SAKG         834

SEQ ID NO: 6           moltype = DNA  length = 2505
FEATURE                Location/Qualifiers
misc_feature           1..2505
                       note = DNA polymerase variant Tth b13
source                 1..2505
                       mol_type = other DNA
                       organism = synthetic construct
SEQUENCE: 6
atggaagcta tgctgccgct gttcgaaccg aaaggtcgtg ttctgctggt tgacggtcac    60
cacctggctt accgtacctt cttcgctctg aaaggtctga ccacctctcg tggtgaaccg   120
gttcaggctg tttacggttt cgctaaatct ctgctgaaag ctctgaaaga agatggttac   180
aaagctgttt tcgttgtatt cgacgcgaaa gctccgtctt ccgtcacga agcttacgaa    240
gcttacaaag ctggtcgtgc tccgaccccg gaagacttcc cgcgtcagct ggctctgatc   300
aaagaactgg ttgacctgct gggtttcacc cgtctggaag ttccgggtta cgaagctgac   360
gacgttctgg ctaccctggc taaaaaagct gaaaaagaag gttacgaagt tcgtatcctg   420
accgctgacc gtgacctgta ccagctggtt tctgaccgtg ttgctgttct gcacccggaa   480
ggtcacctga tcaccccgga atggctgtgg gaaaaatacg gtctgcgtcc ggaacagtgg   540
gttgacttcc gtgctctggt tggtgacccg tctgacaacc tgccgggtgt taaaggtatc   600
ggtgaaaaaa ccgctctgaa actgctgaaa gaatggggtt ctctggaaaa cctgctgaaa   660
aacctggacc gtgttaaacc ggaaaacgtt cgtgaaaaaa tcaaagctca cctggaagac   720
ctgcgtctgt ctctggaact gtctcgtgtt cgtaccgacc tgcctctgga agttgacctg   780
gctcagggtc gtgaaccgga ccgtgaaggt ctgcgtgctt tcctggaact gtctgaattc   840
ggttctctgc tgcacgaatt cggtctgctg gaagctccgg ctccgctgga agaagctccg   900
tggccgcccc cggagggtgc gttcgtcggt ttcgttctgt ctcgtccgga accgatgtgg   960
gctgaactga aagctctggc tgcttgccgt gacggtcgtg ttcaccgtgc tgctgacccg  1020
ctggctggtc tgaaagacct gaaagaagtt cgtggtctgc tgctaaaga cctggctgtt  1080
ctggcttctc gtgaaggtct ggacctggtt ccgggtgacg accctgatgc tgctggcttac 1140
ctgctggacc gtctaacac cacccggaa ggtgttgctc gtcgttacgg tggtgaatgg  1200
accgaagacg ctgctcaccg tgctctgctg tctgaacgtc tgcaccgtaa cctgctgaaa  1260
cgtctggaag gtgaagaaaa actgctgtgg ctgtaccacg aagttgaaaa accgctgtct  1320
cgtgttctgg ctcacatgga agctaccggt gttcgtctta cctgcaggct 1380
ctgtctctgg aactggctga gaaatccgt cgtctggaag aagaagtttt ccgtctggct  1440
ggtcacccgt tcaacctgaa ctcgtgac cagctggaaac gtgttctgtt cgacgaactg  1500
cgtctgccgg ctctgggtaa aacccagaaa accggtaaac gttctacctc tgctgctgtt  1560
ctggaagctc tgcgtgaagc tcacccgatc gttgaaaaaa tcctgcagca ccgtgaactg  1620
accaaaactga aaaacaccta cgttgacccg ctgccctcacc ggtaccggt 1680
cgtctgcaca cccgtttcaa ccagaccgct accgtaccg gtcgtctgtc ttcttctgac  1740
ccgaacctgc agaacatccc ggttcgtacc ccgctgggtc agcgtatccg tcgtgctttc  1800
gttgctgaag ctggttggc tctggttgct ctggactact ctcagatcga actgcgtgtt  1860
ctggctcacc tgtctggtga cgaaaacctg atccgtgttt tccaggaagg taaagacatc  1920
cacacccaga ccgcttcttg gatgttcggt gttccgccgg aagctgttga cccgctgatg  1980
```

```
cgtcgtgctg ctaaaaccgt taacttcggt gttctgtacg gtatgtctgc tcaccgtctg   2040
tctcgtgaac tggctatccc gtacgaagaa gctgttgctt tcatcgaacg ttacttccag   2100
tctttcccga agttcgtgc ttggatcgaa aaaccctgg aagaaggtcg taaacgtggt   2160
tacgttgaaa ccctgttcgg tcgtcgtcgt tacgttccgg acctgaacgc tcgtgttaaa   2220
tctgttcgtg aagctgctga acgtatggct ttcaacatgc cggttcaggg taccgctgct   2280
gacctgatga aactggctat ggttaaactg ttcccgcgtc tgcgtgaaat gggtgctcgt   2340
atgctgctgc aggttcacga cgaactgctg ctggaagctc cgcaggctcg tgctgaagaa   2400
gttgctgctc tggctaaaga agctatggaa aaagcttacc cgctggctgt tccgctggaa   2460
gttgaagttg gtatgggtga agactggctg tctgctaaag gttaa              2505

SEQ ID NO: 7                moltype = AA   length = 834
FEATURE                     Location/Qualifiers
REGION                      1..834
                            note = DNA polymerase variant Tth b46
source                      1..834
                            mol_type = protein
                            organism = synthetic construct
SEQUENCE: 7
MEAMLPLFEP KGRVLLVDGH HLAYRTFFAL KGLTTSRGEP VQAVYGFAKS LLKALKEDGY    60
KAVFVVFDAK APSFRHEAYE AYKAGRAPTP EDFPRQLALI KELVDLLGFT RLEVPGYEAD   120
DVLATLAKKA EKEGYEVRIL TADRDLYQLV SDRVAVLHPE GHLITPEWLW EKYGLRPEQW   180
VDFRALVGDP SDNLPGVKGI GEKTALKLLK EWGSLENLLK NLDRVKPENV REKIKAHLED   240
LRLSLELSRV RTDLPLEVDL AQGREPDREG LRAFLERLEF GSLLHEFGLL EAPAPLEEAP   300
WPPPEGAFVG FVLSRPEPMW AELKALAACR DGRVHRAADP LAGLKDLKEV RGLLAKDLAV   360
LASREGLDLV PGDDPMLLAY LLDPSNTTPE GVARRYGGEW TEDAAHRALL SERLHRNLLK   420
RLEGEEKLLW LYHEVEKPLS RVLAHMEATG VRLDVAYLQA LSLELAEEIR RLEEEVFRLA   480
GHPFNLNSRD QLERVLFDEL RLPALGKTQK TGKRSTSAAV LEALREAHPI VEKILQHREL   540
TKLKNTYVDP LPSLVHPRTG RLHTRFNQTA TATGRLSSSD PNLQNIPVRT PLGQRIRRAF   600
VAEAGWALVA LDYSQIELRV LAHLSGDENL IRVFQEGKDI HTQTASWMFG VPPEAVDPLM   660
RRAAKTVNFG VLYGMSAHRL SQELAIPYRE AVAFIERYFQ SFPKVRAWIE KTLEEGRKRG   720
YVETLFGRRR YVPDLNARVK SVREAAERMA FNMPVQGTAA DLMKLAMVKL FPRLREMGAR   780
MLLQVHDELL LEAPQARAEE VAALAKEAME KAYPLAVPLE VEVGMGEDWL SAKG         834

SEQ ID NO: 8                moltype = DNA   length = 2505
FEATURE                     Location/Qualifiers
misc_feature                1..2505
                            note = DNA polymerase variant Tth b46
source                      1..2505
                            mol_type = other DNA
                            organism = synthetic construct
SEQUENCE: 8
atggaagcta tgctgccgct gttcgaaccg aaaggtcgtg ttctgctggt tgacggtcac     60
cacctggctt accgtacctt cttcgctctg aaaggtctga ccacctctcg tggtgaaccg    120
gttcaggctg tttacggttt cgctaaatct ctgctgaaag ctctgaaaga agatggttac    180
aaagctgttt tcgttgtatt cgacgcgaaa gctccgtctt tccgtcacga agcttacgaa    240
gcttacaaag ctggtcgtgc tccgaccccg gaagacttcc cgcgtcagct ggctctgatc    300
aaagaactgg ttgacctgct gggtttcacc cgtctggaag ttccgggtta cgaagctgac    360
gacgttctgg ctaccctggc taaaaaagct gaaaaagaag gttacgaagt tcgtatcctg    420
accgctgacc gtgacctgta ccagctggtt tctgaccgtg ttgctgttct gcacccggaa    480
ggtcacctga tcaccccgga atggctgtgg gaaaaatacg gtctgcgtcc ggaacagtgg    540
gttgacttcc gtgctctgtt tggtgaccccg tctgcaaacc tgccgggtgt taaaggtatc    600
ggtgaaaaaa ccgctctgaa actgctgaaa gaatgggggtt ctctggaaaa cctgctgaaa    660
aacctggacc gtgttaaacc ggaaaacgtt cgtgaaaaaa tcaaagctca cctggaagac    720
ctgcgtctgt ctctggaact gtctcgtgtt cgtaccgacc tgccgctgga agttgacctg    780
gctcaggggtc gtgaaccgga ccgtgaaggt ctgcgtgctt tcctgcgcctg tctgaaattc    840
ggttctctgc tgcacgaatt cggtctgctg gaagctccgg ctccgctgga agaagctccg    900
tggccgcccc cggagggtgc gttcgtcggc ttcgttctgt ctcgtccgga accgatgtgg    960
gctgaactga aagctctggc tgcttgccgt gacggtcgtg ttcaccgtgc tgctgacccg   1020
ctggctggtc tgaaagacct gaaagaagtt cgtggtctgc tggctaaaga cctggctgtt   1080
ctggctctctc gtgaaggtct ggacctggtt ccgggtgacg acccgatgct gctggcttac   1140
ctgctggacc cgtctaacac caccccggaa ggtgttgctc gtcgttacgg tggtgaatgg   1200
accgaagacg ctgctcaccg tgctctgctg tctgaacgtc tgcaccgtaa cctgctgaaa   1260
cgtctggaag gtgaagaaaa actgctgtgg ctgtaccacg aagttgaaaa accgctgtct   1320
cgtgttctgg ctcacatgga agctaccggt gttcgtctgg acgttgctta cctgcaggct   1380
ctgtctctgg aactggctga agaaatccgt cgtctggaag aagaagtttt ccgtctggct   1440
ggtcacccgt tcaacctgaa ctcgtgtgac cagctggaac gtgttctgtt cgacgaactg   1500
cgtctgccgg ctctgggtaa aacccagaaa accggtaaac gttctacctc tgctgctgtt   1560
ctggaagctc tgcgtgaagc tcacccgatc gttgaaaaaa tcctgcagca ccgtgaactg   1620
accaaactga aaaacaccta cgttgacccg ctgccgtctc tggttcaccc gcgtaccggt   1680
cgtctgcaca cccgtttcaa ccagaccgct accgctaccg gtcgtctgtc ttcttctgac   1740
ccgaacctgc agaacatccc ggttcgtacc ccgctgggtc agcgtatccg tcgtgctttc   1800
gttgctgaag ctggttgggc tctggttgct ctggactact ctcagatcga actgcgtgtt   1860
ctggctcacc tgtctggtga cgaaaacctg atccgtgttt tccaggaagg taaagacatc   1920
cacacccaga ccgcttcttg gatgttcggt gttccgccag aagctgttga cccgctgatg   1980
cgtcgtgctg ctaaaaccgt taacttcggt gttctgtacg gtatgtctgc tcaccgtctg   2040
tctcaggaac tggctatccc gtaccgtgaa gctgttgctt tcatcgaacg ttacttccag   2100
tctttcccga agttcgtgc ttggatcgaa aaaccctgg aagaaggtcg taaacgtggt   2160
tacgttgaaa ccctgttcgg tcgtcgtcgt tacgttccgg acctgaacgc tcgtgttaaa   2220
tctgttcgtg aagctgctga acgtatggct ttcaacatgc cggttcaggg taccgctgct   2280
```

```
gacctgatga aactggctat ggttaaactg ttcccgcgtc tgcgtgaaat gggtgctcgt    2340
atgctgctgc aggttcacga cgaactgctg ctggaagctc cgcaggctcg tgctgaagaa    2400
gttgctgctc tggctaaaga agctatgaa  aaagcttacc cgctggctgt tccgctggaa    2460
gttgaagttg gtatgggtga agactggctg tctgctaaag gttaa                    2505
```

```
SEQ ID NO: 9              moltype = AA   length = 834
FEATURE                   Location/Qualifiers
REGION                    1..834
                          note = DNA polymerase variant Tth b13 b46
source                    1..834
                          mol_type = protein
                          organism = synthetic construct
SEQUENCE: 9
MEAMLPLFEP KGRVLLVDGH HLAYRTFFAL KGLTTSRGEP VQAVYGFAKS LLKALKEDGY    60
KAVFVVFDAK APSFRHEAYE AYKAGRAPTP EDFPRQLALI KELVDLLGFT RLEVPGYEAD    120
DVLATLAKKA EKEGYEVRIL TADRDLYQLV SDRVAVLHPE GHLITPEWLW EKYGLRPEQW    180
VDFRALVGDP SDNLPGVKGI GEKTALKLLK EWGSLENLLK NLDRVKPENV REKIKAHLED    240
LRLSLELSRV RTDLPLEVDL AQGREPDREG LRAFLERLEF GSLLHEFGLL EAPAPLEEAP    300
WPPPEGAFVG FVLSRPEPMW AELKALAACR DGRVHRAADP LAGLKDLKEV RGLLAKDLAV    360
LASREGLDLV PGDDPMLLAY LLDPSNTTPE GVARRYGGEW TEDAAHRALL SERLHRNLLK    420
RLEGEEKLLW LYHEVEKPLS RVLAHMEATG VRLDVAYLQA LSLELAEEIR RLEEEVFRLA    480
GHPFNLNSRD QLERVLFDEL RLPALGKTQK TGKRSTSAAV LEALREAHPI VEKILQHREL    540
TKLKNTYVDP LPSLVHPRTG RLHTRFNQTA TATGRLSSSD PNLQNIPVRT PLGQRIRRAF    600
VAEAGWALVA LDYSQIELRV LAHLSGDENL IRVFQEGKDI HTQTASWMFG VPPEAVDPLM    660
RRAAKTVNFG VLYGMSAHRL SRELAIPYRE AVAFIERYFQ SFPKVRAWIE KTLEEGRKRG    720
YVETLFGRRR YVPDLNARVK SVREAAERMA FNMPVQGTAA DLMKLAMVKL FPRLREMGAR    780
MLLQVHDELL LEAPQARAEE VAALAKEAME KAYPLAVPLE VEVGMGEDWL SAKG          834
```

```
SEQ ID NO: 10             moltype = DNA   length = 2505
FEATURE                   Location/Qualifiers
misc_feature              1..2505
                          note = DNA polymerase variant Tth b13 b46
source                    1..2505
                          mol_type = other DNA
                          organism = synthetic construct
SEQUENCE: 10
atggaagcta tgctgccgct gttcgaaccg aaaggtcgtg ttctgctggt tgacggtcac    60
cacctggctt accgtacctt cttcgctctg aaaggtctga ccacctctcg tggtgaaccg    120
gttcaggctg tttacggttt cgctaaatct ctgctgaaag ctctgaaaga agatggttac    180
aaagctgttt tcgttgtatt cgacgcgaaa gctccgtctt ccgtcacgaa gcttacgaa    240
gcttacaaag ctggtcgtgc tccgacccg  gaagacttcc cgcgtcagct ggctctgatc    300
aaagaactgg ttgacctgct gggttcacc  cgtctggaag ttccgggtta cgaagctgac    360
gacgttctgg ctaccctggc taaaaaagct gaaaaggaag gttacgaagt tcgtatcctg    420
accgctgacc gtgacctgta ccagctggtt tctgaccgtg ttgctgttct gcacccggaa    480
ggtcacctga tcaccccgga atggctgtgg gaaaaatacg gtctgcgtcc ggaacagtgg    540
gttgacttcc gtgctctggt tggtgacccg tctgacaacc tgccgggtgt taaaggtatc    600
ggtgaaaaaa ccgctctgaa actgctgaaa gaatggggtt ctctggaaaa cctgctgaaa    660
aacctggacc gtgttaaacc ggaaaacgtt cgtgaaaaaa tcaaagctca cctggaagac    720
ctgcgtctgt ctctggaact gtcccgtgtt cgtaccgacc tgccgctgga agttgacctg    780
gctcaggtc  gtgaaccgga ccgtgaaggt ctgcgtgctt tcctggaacg tctggaattc    840
ggttctctgc tgcacgaatt cggtctgctg gaagctccag ctccgctgga agaagctccg    900
tggccgcccc cggagggtgc gttcgtcggc ttcgttctgt ctcgtccgga accgatgtgg    960
gctgaactga agctctggc  tgcttgccgt gacggtcgtg ttcaccgtgc tgctgacccg    1020
ctggctggtc tgaaagacct gaaagaagtt cgtggtctgc tggctaaaga cctggctgtt    1080
ctggccttctc gtgaaggtct ggacgatgct cgggtgacg  acccgatgct gcttggcttc    1140
ctgctggacc cgtctaacac caccccggaa ggtgttgctc gtcgttacg  tggtgaatgg    1200
accgaagacg ctgctcaccg tgctctgctg tctgaacgtc tgcaccgtaa cctgctgaaa    1260
cgtctggaag tgaagaaaa  actgctgtgg ctgtaccacg aagttgaaaa accgctgtct    1320
cgtgttctgg ctcacatgga agctaccggt gttcgtctgg acgttgctta cctgcaggct    1380
ctgtctctgg aactggctga agaaatccgt cgtctggaaa aagaagtttt ccgtctggct    1440
ggtcacccgt tcaacctgaa ctctcgtgac cagctggaac gtgttctgtt cgacgaactg    1500
cgtctgccgc ctctgggtaa aacccagaaa accgtaaac  gttctacctc tgctgctgtt    1560
ctggaagctc tgcgtgaagc tcacccgatc gttgaaaaaa tcctgcagca ccgtgaactg    1620
accaaactga aaaacaccta cgttgacccg ctgccgtctc tggttcaccc gcgtaccggt    1680
cgtctgcaca cccgtttcaa ccagaccgct accgctaccg gtcgtctgtc ttcttctgac    1740
ccgaacctgc agaacatccc ggttcgtacc ccgctgggtc agcgtatccg tcgtgctttc    1800
gttgctgaag ctggttgggc tctggttgct ctggactact ctcagatcga actgcgtgtt    1860
ctggctcacc tgtctggtga cgaaaacctg atccgtgttt tccaggaagg taaagacatc    1920
cacacccaga ccgcttcttg gatgttcggt gttccgccga agctgttga  cccgctgatg    1980
cgtcgtgctg ctaaaaccgt taacttcggt gttctgtacg gtatgtctgc tcaccgtctg    2040
tctcgtgaac tggctatccc gtaccgtgaa gctgttgctt tcatcgaacg ttacttccag    2100
tctttcccga aagttcgtgc ttggatcgaa aaaccctgg  aagaaggtcg taaacgtggt    2160
tacgttgaaa ccctgttcgg tcgtcgtcgt acgttccgg  acctgaacgc tcgtgttaaa    2220
tctgttcgtg aagctgctga acgtatggct ttcaacatgc cggttcaggg tacggctgct    2280
gacctgatga aactggctat ggttaaactg ttcccgcgtc tgcgtgaaat gggtgctcgt    2340
atgctgctgc aggttcacga cgaactgctg ctggaagctc cgcaggctcg tgctgaagaa    2400
gttgctgctc tggctaaaga agctatgaa  aaagcttacc cgctggctgt tccgctggaa    2460
gttgaagttg gtatgggtga agactggctg tctgctaaag gttaa                    2505
```

```
SEQ ID NO: 11            moltype = AA   length = 911
FEATURE                  Location/Qualifiers
REGION                   1..911
                         note = PIP-L14-PIP-L14-PIP-L15 Tth
source                   1..911
                         mol_type = protein
                         organism = synthetic construct
SEQUENCE: 11
MSGKQATLFD FLKSGSGSGS GSGSGSGKQA TLFDFLKSGS GSGSGSGSGS GKQATLFDFL    60
KKGSGSGSGS GSGSGSGMEA MLPLFEPKGR VLLVDGHHLA YRTFFALKGL TTSRGEPVQA   120
VYGFAKSLLK ALKEDGYKAV FVVFDAKAPS FRHEAYEAYK AGRAPTPEDF PRQLALIKEL   180
VDLLGFTRLE VPGYEADDVL ATLAKKAEKE GYEVRILTAD RDLYQLVSDR VAVLHPEGHL   240
ITPEWLWEKY GLRPEQWVDF RALVGDPSDN LPGVKGIGEK TALKLLKEWG SLENLLKNLD   300
RVKPENVREK IKAHLEDLRL SLELSRVRTD LPLEVDLAQG REPDREGLRA FLERLEFGSL   360
LHEFGLLEAP APLEEAPWPP PEGAFVGFVL SRPEPMWAEL KALAACRDGR VHRAADPLAG   420
LKDLKEVRGL LAKDLAVLAS REGLDLVPGD DPMLLAYLLD PSNTTPEGVA RRYGGEWTED   480
AAHRALLSER LHRNLLKRLE GEEKLLWLYH EVEKPLSRVL AHMEATGVRL DVAYLQALSL   540
ELAEEIRRLE EEVFRLAGHP FNLNSRDQLE RVLFDELRLP ALGKTQKTGK RSTSAAVLEA   600
LREAHPIVEK ILQHRELTKL KNTYVDPLPS LVHPRTGRLH TRFNQTATAT GRLSSSDPNL   660
QNIPVRTPLG QRIRRAFVAE AGWALVALDY SQIELRVLAH LSGDENLIRV FQEGKDIHTQ   720
TASWMFGVPP EAVDPLMRRA AKTVNFGVLY GMSAHRLSQE LAIPYEEAVA FIERYFQSFP   780
KVRAWIEKTL EEGRKRGYVE TLFGRRRYVP DLNARVKSVR EAAERMAFNM PVQGTAADLM   840
KLAMVKLFPR LREMGARMLL QVHDELLLEA PQARAEEVAA LAKEAMEKAY PLAVPLEVEV   900
GMGEDWLSAK G                                                      911

SEQ ID NO: 12            moltype = DNA   length = 20
FEATURE                  Location/Qualifiers
variation                12
                         note = n is a, c, g, or t
source                   1..20
                         mol_type = other DNA
                         organism = synthetic construct
SEQUENCE: 12
cgytggatgc gnttycatga                                              20

SEQ ID NO: 13            moltype = DNA   length = 22
FEATURE                  Location/Qualifiers
misc_feature             1..22
                         note = PCR Reverse Primer COG1R
source                   1..22
                         mol_type = other DNA
                         organism = synthetic construct
SEQUENCE: 13
cttagacgcc atcatcatty ac                                           22

SEQ ID NO: 14            moltype = DNA   length = 26
FEATURE                  Location/Qualifiers
variation                9
                         note = n is a, c, g, or t
source                   1..26
                         mol_type = other DNA
                         organism = synthetic construct
SEQUENCE: 14
cargarbcna tgttyagrtg gatgag                                       26

SEQ ID NO: 15            moltype = DNA   length = 21
FEATURE                  Location/Qualifiers
misc_feature             1..21
                         note = PCR Reverse Primer COG2R
source                   1..21
                         mol_type = other DNA
                         organism = synthetic construct
SEQUENCE: 15
tcgacgccat cttcattcac a                                            21

SEQ ID NO: 16            moltype = DNA   length = 20
FEATURE                  Location/Qualifiers
misc_feature             1..20
                         note = Probe RING1-TP(a). 5'-end is labeled Cy5 and 3'-end
                          is labeled BHQ3
source                   1..20
                         mol_type = other DNA
                         organism = synthetic construct
SEQUENCE: 16
agatygcgat cycctgtcca                                              20

SEQ ID NO: 17            moltype = DNA   length = 20
FEATURE                  Location/Qualifiers
misc_feature             1..20
```

```
                        note = Probe RING2AL-TP. 5'end is labeled ROX and 3'-end is
                         labeled BHQ2
source                  1..20
                        mol_type = other DNA
                        organism = synthetic construct
SEQUENCE: 17
tgggaggggsg atcgcratct                                                        20

SEQ ID NO: 18           moltype = AA  length = 12
FEATURE                 Location/Qualifiers
REGION                  1..12
                        note = A partial sequence (A1-A12) of Tth DNA polymerase
source                  1..12
                        mol_type = protein
                        organism = synthetic construct
SEQUENCE: 18
LSQELAIPYE EA                                                                 12

SEQ ID NO: 19           moltype = AA  length = 12
FEATURE                 Location/Qualifiers
REGION                  1..12
                        note = A partial sequence (A1-A12) of Tth DNA polymerase
                         variant
source                  1..12
                        mol_type = protein
                        organism = synthetic construct
SEQUENCE: 19
LSRELAIPYR EA                                                                 12

SEQ ID NO: 20           moltype = AA  length = 12
FEATURE                 Location/Qualifiers
REGION                  1..12
                        note = A partial sequence (A1-A12) of Bca polymerase
source                  1..12
                        mol_type = protein
                        organism = synthetic construct
SEQUENCE: 20
LAQNLNISRK EA                                                                 12

SEQ ID NO: 21           moltype = AA  length = 12
FEATURE                 Location/Qualifiers
REGION                  1..12
                        note = A partial sequence (A1-A12) of Bst polymerase
source                  1..12
                        mol_type = protein
                        organism = synthetic construct
SEQUENCE: 21
LAQNLNITRK EA                                                                 12

SEQ ID NO: 22           moltype = AA  length = 12
FEATURE                 Location/Qualifiers
REGION                  1..12
                        note = A partial sequence (A1-A12) of Aac polymerase
source                  1..12
                        mol_type = protein
                        organism = synthetic construct
SEQUENCE: 22
LAQNLNIPQK EA                                                                 12

SEQ ID NO: 23           moltype = AA  length = 592
FEATURE                 Location/Qualifiers
REGION                  1..592
                        note = DNA polymerase I Bacillus caldotenax
source                  1..592
                        mol_type = protein
                        organism = synthetic construct
SEQUENCE: 23
MESPSSEEEK PLAKMAFTLA DRVTEEMLAD KAALVVEVVE ENYHDAPIVG IAVVNEHGRF              60
FLRPETALAD PQFVAWLGDE TKKKSMFDSK RAAVALKWKG IELCGVSFDL LLAAYLLDPA              120
QGVDDVAAAA KMKQYEAVRP DEAVYGKGAK RAVPDEPVLA EHLVRKAAAI WALERPFLDE              180
LRRNEQDRLL VELEQPLSSI LAEMEFAGVK VDTKRLEQMG EELAEQLRTV EQRIYELAGQ              240
EFNINSPKQL GVILFEKLQL PVLKKTKTGY STSADVLEKL APYHEIVENI LHYRQLGKLQ              300
STYIEGLLKV VRPDTKKVHT IFNQALTQTG RLSSTEPNLQ NIPIRLEEGR KIRQAFVPSE              360
SDWLIFAADY SQIELRVLAH IAEDDNLMEA FRRDLDIHTK TAMDIFQVSE DEVTPNMRRQ              420
AKAVNFGIVY GISDYGLAQN LNISRKEAAE FIERYFESFP GVKRYMENIV QEAKQKGYVT              480
TLLHRRRYLP DITSRNFNVR SFAERMAMNT PIQGSAADII KKAMIDLNAR LKEERLQARL              540
LLQVHDELIL EAPKEEMERL CRLVPEVMEQ AVTLRVPLKV DYHYGSTWYD AK                     592

SEQ ID NO: 24           moltype = AA  length = 609
```

```
FEATURE                 Location/Qualifiers
REGION                  1..609
                        note = DNA polymerase I Alicyclobacillus acidocaldarius
source                  1..609
                        mol_type = protein
                        organism = synthetic construct
SEQUENCE: 24
MELDFRSLVD KISEEMSHDS TPTPSPAAAS GASSEWSSFA YGLIEDAGAW QEAISSFSEP    60
VGVMMDLADP DYHRAEIRGM AVATPKRAYY VRFGERLELS DVRPWLVSDR PKVAFDLKSM   120
AFALDAHGIG LTSECGWQDV KLAAYLLNPQ DGEVELSDVF ARERGQELPA WEEGEREKWL   180
AYTASQLPPL FESLAYTIRM QEMERLYQEV ELPLAFVLAK MEITGFYVNR EKLVAFGQEL   240
TERIKRITQE IYDLAGTSFN LNSPKQLGEI LFDKLGLPAL KKTKTGYSTS ADVLEKLAPM   300
HEIVQKILDY RLLAKLQSTY VEGLLKVIRK ETGRVHTRFH QTLTATGRLS SSEPNLQNIP   360
IRLEEGRRLR QVFEPTYKDW VIFAADYSQI ELRILAHLSG DEALIDAFRR DMDIHTRTAA   420
DVFEVPPEQV TSLMRRQAKA VNFGIVYGIS DFGLAQNLNI PQKEAKRFIE SYFEKFPGVK   480
RYMDEIVKQA RERGYVTTLM NRRRYLPDIH SRNYQLRSFA ERTAMNTPIQ GSAADLIKLA   540
MVRIDRAMRD AQMDARMLLQ VHDELIFECP KDELAALEVL VRDNMENAMT LSVPLKVDTA   600
YGPTWYDAK                                                          609

SEQ ID NO: 25           moltype = AA  length = 832
FEATURE                 Location/Qualifiers
REGION                  1..832
                        note = DNA polymerase I Thermus aquaticus
source                  1..832
                        mol_type = protein
                        organism = synthetic construct
SEQUENCE: 25
MRGMLPLFEP KGRVLLVDGH HLAYRTFHAL KGLTTSRGEP VQAVYGFAKS LLKALKEDGD    60
AVIVVFDAKA PSFRHEAYGG YKAGRAPTPE DFPRQLALIK ELVDLLGLAR LEVPGYEADD   120
VLASLAKKAE KEGYEVRILT ADKDLYQLLS DRIHALHPEG YLITPAWLWE KYGLRPDQWA   180
DYRALTGDES DNLPGVKGIG EKTARKLLEE WGSLEALLKN LDRLKPAIRE KILAHMDDLK   240
LSWDLAKVRT DLPLEVDFAK RREPDRERLR AFLERLEFGS LLHEFGLLES PKALEEAPWP   300
PPEGAFVGFV LSRKEPMWAD LLALAAARGG RVHRAPEPYK ALRDLKEARG LLAKDLSVLA   360
LREGLGLPPG DDPMLLAYLL DPSNTTPEGV ARRYGGEWTE EAGERAALSE RLFANLWGRL   420
EGEERLLWLY REVERPLSAV LAHMEATGVR LDVAYLRALS LEVAEEIARL EAEVFRLAGH   480
PFNLNSRDQL ERVLFDELGL PAIGKTEKTG KRSTSAAVLE ALREAHPIVE KILQYRELTK   540
LKSTYIDPLP DLIHPRTGRL HTRFNQTATA TGRLSSSDPN LQNIPVRTPL GQRIRRAFIA   600
EEGWLLVALD YSQIELRVLA HLSGDENLIR VFQEGRDIHT ETASWMFGVP REAVDPLMRR   660
AAKTINFGVL YGMSAHRLSQ ELAIPYEEAQ AFIERYFQSF PKVRAWIEKT LEEGRRRGYV   720
ETLFGRRRYV PDLEARVKSV REAAERMAFN MPVQGTAADL MKLAMVKLFP RLEEMGARML   780
LQVHDELVLE APKERAEAVA RLAKEVMEGV YPLAVPLEVE VGIGEDWLSA KE           832

SEQ ID NO: 26           moltype = DNA  length = 19
FEATURE                 Location/Qualifiers
misc_feature            1..19
                        note = PCR forward Primer hACTB-F
source                  1..19
                        mol_type = other DNA
                        organism = synthetic construct
SEQUENCE: 26
tggcacccag cacaatgaa                                                19

SEQ ID NO: 27           moltype = DNA  length = 20
FEATURE                 Location/Qualifiers
misc_feature            1..20
                        note = PCR Reverse Primer hACTB-533
source                  1..20
                        mol_type = other DNA
                        organism = synthetic construct
SEQUENCE: 27
atcacctccc ctgtgtggac                                               20

SEQ ID NO: 28           moltype = AA  length = 954
FEATURE                 Location/Qualifiers
source                  1..954
                        mol_type = protein
                        organism = Geobacillus stearothermophilus
SEQUENCE: 28
MASTRRAAAT QAGRAGPFDR QALGRGASRL HYGDERSRAR HRVYDSFPEA GAVAGFFLWP    60
PPAWYNRTRN VRGGMMLKNK LVLIDGNSVA YRAFFALPLL HNDKGIHTNA VYGFTMMLNK   120
ILAEEQPTHI LVAFDAGKTT FRHETFQDYK GGRQQTPPEL SEQFPLVREL LKAYRIPAYE   180
LDHYEADDII GTMAARAERE GFAVKVISGD RDLTQLASPQ VTVEITKKGI TDIESYTPET   240
VVEKYGLTPE QIVDLKGLMG DKSDNIPGVP GIGKKTAVKL LKQFGTVENV LASIDEIKGE   300
KLKENLRQYR DLALLSKQLA AICRDAPVEL TLDDIVYKGE DREKVVALFQ ELGFQSFLDK   360
MAVQTDEGEK PLAGMDFAIA DSVTDEMLAD KAALVVEVVG DNYHHAPIVG IALANERGRF   420
FLRPETAVAD PKFLAWLGDE TKKKTMFDSK RAAVALNGKG IELAGVGVVF DLLLAAYLLD   480
PAQAAGDVAA VAKMHQYEAV RSDEAVYGKG AKRTVPDEPT LAEQLVRKAA AIWALEEPLM   540
DELRRNEQDR LLTELEHALA GILANMEFTG VKVDTKRLEQ MGAELTEQLQ AVERRIYELA   600
GQEFNINSPK QLGTVLFDKL QLPVLKKTKT GYSTSADVLE KLAPHHEIVE HILHYRQLGK   660
```

```
LQSTYIEGLL KVVHPVTGKV HTMFNQALTQ TGRLSSVEPN LQNIPIRLEE GRKIRQAFVP   720
SEPDWLIFAA DYSQIELRVL AHIAEDDNLI EAFRRWLDIH TKTAMDIFHV SEEDVTANMR   780
RQAKAVNFGI VYGISDYGLA QNLNITRKEA AEFIERYFAS FPGVKQYMDN IVQEAKQKGY   840
VTTLLHRRRY LPDITSRNFN VRTFAERTAM NTPIQGSAAD IIKKAMIDLS VSVREERLQA   900
RLLLQGHDEL ILEAPKEEIG RLCRLVPEVM EQAVTLRVPL KVDYHYGPTW YDAK         954
```

DNA POLYMERASE MUTANT SUITED TO NUCLEIC ACID AMPLIFICATION FROM RNA

REFERENCE TO AN ELECTRONIC SEQUENCE LISTING

The contents of the electronic sequence listing (Attach-B_SequenceListing-0360A.xml; Size: 50,589 bytes; and Date of Creation: Jun. 11, 2024) is herein incorporated by reference in its entirety.

TECHNICAL FIELD

The present invention relates to a DNA polymerase mutant suitable for nucleic acid amplification reaction from RNA. Furthermore, the present invention relates to a method for enhancing the activity of an existing DNA polymerase on nucleic acid amplification from RNA, and a method for producing a DNA polymerase mutant suitable for nucleic acid amplification reaction from RNA.

BACKGROUND ART

DNA polymerases play a central role in accurately transmitting genetic information from generation to generation, that is, in replication and retention of genomes. DNA polymerases function intracellularly as an enzyme responsible for DNA synthesis, and polymerize deoxyribonucleoside triphosphates in the presence of metal activators such as $Mg^{2+}$ on an order required for replication of a DNA template or a polynucleotide template. DNA polymerases are involved in a series of DNA synthesis processes including DNA replication, DNA repair, recombination and gene amplification in vivo. During the DNA synthesis processes, the DNA template is replicated once or several times to produce identical replicas. In contrast, DNA replication can be repeated many times in vitro, for example in a polymerase chain reaction.

So-called reverse transcription polymerase chain reaction (RT-PCR) is a technique for detecting or quantifying a target RNA by amplification and used in many applications. In order to amplify a target RNA by PCR, an RNA template first needs to be reverse transcribed to cDNA. A typical RT-PCR method is performed by using a reverse transcriptase for synthesizing cDNA from an RNA template and a heat-resistant DNA polymerase for performing nucleic acid amplification from the synthesized cDNA as a template. In such a case, it is necessary to select a reaction solution composition suitable for both the reverse transcriptase and the heat-resistant DNA polymerase to be used. In some cases, the lid of a reaction tube may be opened between the reverse transcription reaction and the subsequent nucleic acid amplification reaction, and the risk of cross-contamination cannot be ignored. Thus, a one-step RT-PCR method has been developed for performing a reverse transcription reaction and PCR continuously without opening a reaction vessel. In this method, a DNA polymerase having a reverse transcriptase activity may be used. However, since a reverse transcription reaction and PCR are performed using the same reaction solution composition, it is necessary to balance the reverse transcription reaction and PCR. Further, a technique for enhancing the reverse transcription efficiency when the reverse transcription reaction and PCR are performed in the same reaction solution composition has been reported. (See Patent Literatures 1 to 3).

In recent years, various isothermal nucleic acid amplification reaction methods have been proposed and put into practical use. The isothermal nucleic acid amplification methods are also often used in combination with a reverse transcription reaction using an RNA as a template, and the same problem as RT-PCR methods as described above has arisen. In other words, also for the RT-isothermal nucleic acid amplification methods, it is necessary to perform a reverse transcription reaction and isothermal nucleic acid amplification in the same reaction solution composition and balance the reverse transcription reaction and the isothermal nucleic acid amplification.

CITATION LIST

Patent Literatures

Patent Literature 1: JP-B 3844975
Patent Literature 2: WO2012/139748
Patent Literature 3: WO2014/090836

SUMMARY OF INVENTION

Problem to be Solved by the Invention

An object of the present invention to provide a genetic engineering improvement method for creating a DNA polymerase having a reverse transcriptase activity which is suitable for performing a reverse transcription reaction and a nucleic acid amplification reaction in the same container.

Solution for Problem

The present inventors diligently studied to develop a DNA polymerase mutant having a reverse transcriptase activity which is suitable for performing a reverse transcription reaction and a nucleic acid amplification reaction. As a result, the present inventors surprisingly succeeded in finding a method of producing a DNA polymerase mutant having a reverse transcriptase activity that is superior to conventional techniques by introducing a mutation into a specific position in an amino acid sequence. Thus the present invention was completed.

The first embodiment of the present invention relates to a mutant of DNA polymerase having a reverse a transcriptase activity and comprising a sequence consisting of 12 amino acids A1-A12:

A1 is a branched chain amino acid residue,
A2 is a hydrophilic neutral amino acid residue or a hydrophobic aliphatic amino acid residue,
A3 is a hydrophilic neutral amino acid residue,
A4 is an acidic amino acid residue or a hydrophilic neutral amino acid residue,
A5 is a branched chain amino acid residue,
A6 is a hydrophobic aliphatic amino acid residue or a hydrophilic neutral amino acid residue,
A7 is a branched chain amino acid residue,
A8 is a proline residue or a hydrophilic neutral amino acid residue,
A9 is a hydrophobic aromatic amino acid residue, a basic amino acid residue, or a hydrophilic neutral amino acid residue,
A10 is an acidic amino acid residue or a basic amino acid residue,
A11 is an acidic amino acid residue, and
A12 is a hydrophobic aliphatic amino acid residue;
wherein A3 and/or A10 is replaced by a basic amino acid residue that is different from the amino acid residue before introduction of mutation.

In the DNA polymerase mutant having a reverse transcriptase activity of the first embodiment of the present invention, the sequence consisting of 12 amino acids before introduction of mutation preferably comprises leucine as A1, glutamine as A3, leucine as A5, isoleucine as A7, glutamic acid as A11 and alanine as A12. In the DNA polymerase mutant having a reverse transcriptase activity of the first embodiment of the present invention, A3 and/or A10 in the sequence consisting of 12 amino acids is preferably replaced by an amino acid selected from the group consisting of lysine, arginine and histidine. For example, it is preferable that A3 and/or A10 is replaced by arginine.

The DNA polymerase mutant having a reverse transcriptase activity of the first embodiment of the present invention may be derived from any DNA polymerase that is not particularly limited, as long as the mutant is derived from a DNA polymerase having a reverse transcriptase activity that is suitable for performing a reverse transcription reaction and a nucleic acid amplification reaction in the same container. For example, the DNA polymerase mutant of the present invention is preferably derived from a DNA polymerase from *Thermus thermophilus*, a DNA polymerase from *Thermus aquaticus*, a DNA polymerase from *Bacillus cardotenax*, a DNA polymerase from *Bacillus stearothermophilus*, or a DNA polymerase from *Alicyclobacillus acidocaldarius*.

The second embodiment of the present invention relates to a kit containing the DNA polymerase mutant having a reverse transcriptase activity of the first embodiment of the present invention. The kit may contain various components as a kit for preparing a reaction solution suitable for a reverse transcription reaction and a nucleic acid amplification reaction as described later.

The third embodiment of the present invention relates to a composition comprising the DNA polymerase mutant having a reverse transcriptase activity of the first embodiment of the present invention. The composition may comprise various components as a composition suitable for a reverse transcription reaction and a nucleic acid amplification reaction as described later.

The fourth embodiment of the present invention relates to a method for producing a DNA polymerase having a reverse transcriptase activity suitable for nucleic acid amplification from an RNA, the method comprising:

(1) a step of selecting a DNA polymerase comprising a sequence consisting of 12 amino acids A1-A12:
   A1 is a branched chain amino acid residue,
   A2 is a hydrophilic neutral amino acid residue or a hydrophobic aliphatic amino acid residue, A3 is a hydrophilic neutral amino acid residue,
   A4 is an acidic amino acid residue or a hydrophilic neutral amino acid residue,
   A5 is a branched chain amino acid residue,
   A6 is a hydrophobic aliphatic amino acid residue or a hydrophilic neutral amino acid residue,
   A7 is a branched chain amino acid residue,
   A8 is a proline residue or a hydrophilic neutral amino acid residue,
   A9 is a hydrophobic aromatic amino acid residue, a basic amino acid residue, or a hydrophilic neutral amino acid residue,
   A10 is an acidic amino acid residue or a basic amino acid residue,
   A11 is an acidic amino acid residue, and
   A12 is a hydrophobic aliphatic amino acid residue; and (2) a step of replacing A3 and/or A10 in the sequence consisting of 12 amino acids of the DNA polymerase selected in step (1) by a basic amino acid residue that is different from the amino acid residue before introduction of mutation.

In the production method of the fourth embodiment of the present invention, the DNA polymerase selected in step (1) may comprise the sequence consisting of 12 amino acids in which A1 is leucine, A3 is glutamine, A5 is leucine, A7 is isoleucine, A11 is glutamic acid and A12 is alanine. In step (2), A3 and/or A10 may be replaced by an amino acid selected from the group consisting of lysine, arginine and histidine.

The production method of the fourth embodiment of the present invention may be combined with a method comprising producing nucleic acid encoding the mutant and then introducing the nucleic acid into an appropriate host to express the mutant.

The fifth embodiment of the present invention relates to a method for improving a DNA polymerase having a reverse transcriptase activity and comprising a sequence consisting of 12 amino acids A1-A12:
   A1 is a branched chain amino acid residue,
   A2 is a hydrophilic neutral amino acid residue or a hydrophobic aliphatic amino acid residue,
   A3 is a hydrophilic neutral amino acid residue,
   A4 is an acidic amino acid residue or a hydrophilic neutral amino acid residue,
   A5 is a branched chain amino acid residue,
   A6 is a hydrophobic aliphatic amino acid residue or a hydrophilic neutral amino acid residue,
   A7 is a branched chain amino acid residue,
   A8 is a proline residue or a hydrophilic neutral amino acid residue,
   A9 is a hydrophobic aromatic amino acid residue, a basic amino acid residue, or a hydrophilic neutral amino acid residue,
   A10 is an acidic amino acid residue or a basic amino acid residue,
   A11 is an acidic amino acid residue, and
   A12 is a hydrophobic aliphatic amino acid residue; the method comprising replacing A3 and/or A10 by another basic amino acid residue.

In the improvement method of the fifth embodiment of the present invention, as the DNA polymerase having a reverse transcriptase activity, for example, a DNA polymerase comprising the sequence consisting of 12 amino acids in which A1 is leucine, A3 is glutamine, A5 is leucine, A7 is isoleucine, A11 is glutamic acid and A12 are alanine can be selected. Further, in the improvement method of the fifth embodiment of the present invention, A3 and/or A10 in the sequence consisting of 12 amino acids may be replaced, for example, by an amino acid selected from the group consisting of lysine, arginine and histidine.

In the first to fifth embodiments of the present invention, it is preferable that the DNA polymerase having a reverse transcriptase activity comprises a sequence consisting of 12 amino acids A1-A12:
   A1 is leucine,
   A2 is serine or alanine,
   A3 is glutamine,
   A4 is glutamic acid or asparagine,
   A5 is leucine,
   A6 is alanine or asparagine,
   A7 is isoleucine,
   A8 is proline, serine or threonine,
   A9 is tyrosine, arginine or glutamine, A10 is glutamic acid or lysine, A11 is glutamic acid, and A12 is alanine; and in the mutant, A3 and/or A10 is replaced by a basic amino acid residue that is different from the amino acid residue before introduction of mutation. For example, in the DNA polymerase mutant, A3 and/or A10 may be replaced by an amino acid selected from the group consisting of lysine, arginine and histidine.

Effects of the Invention

The present invention provides a DNA polymerase mutant having a reverse transcriptase activity which is suitable for performing a reverse transcription reaction and a nucleic acid amplification reaction in the same container, and a method for producing the mutant. According to the present invention, introduction of mutation as described in the present invention can be performed in any DNA polymerase having a reverse transcriptase activity and comprising a specific partial amino acid sequence shown by A1-A12 as described above. As a result, the time required for a reverse transcription reaction can be shortened as compared to conventional methods, DNA can be generated in a sufficient amount for a starting template in the subsequent nucleic acid amplification reaction, and the reverse transcriptase reaction and the nucleic acid amplification reaction can be achieved with higher detection sensitivity than conventional methods in a short time.

MODE FOR CARRYING OUT THE INVENTION

1. DNA Polymerase Mutant Having Reverse Transcriptase Activity of the Present Invention The first aspect of the present invention relates to a DNA polymerase mutant suitable for a reverse transcriptase reaction and a nucleic acid amplification reaction. The mutant of the present invention is a mutant of a DNA polymerase having a reverse transcriptase activity that comprises a sequence consisting of 12 amino acids A1-A12:

A1 is a branched chain amino acid residue;

A2 is a hydrophilic neutral amino acid residue or a hydrophobic aliphatic amino acid residue;

A3 is a hydrophilic neutral amino acid residue;

A4 is an acidic amino acid residue or a hydrophilic neutral amino acid residue;

A5 is a branched chain amino acid residue;

A6 is a hydrophobic aliphatic amino acid residue or a hydrophilic neutral amino acid residue;

A7 is a branched chain amino acid residue;

A8 is a proline residue or a hydrophilic neutral amino acid residue;

A9 is a hydrophobic aromatic amino acid residue, a basic amino acid residue, or a hydrophilic neutral amino acid residue;

A10 is an acidic amino acid residue or a basic amino acid residue;

A11 is an acidic amino acid residue; and

A12 is a hydrophobic aliphatic amino acid residue; wherein in the mutant, A3 and/or A10 is replaced by another basic amino acid residue.

The mutant comprising the constitution as described above is a DNA polymerase mutant suitable for a reverse transcription reaction and a nucleic acid amplification reaction performed in one container.

As used herein, examples of the "branched chain amino acid residue" include a valine residue, an isoleucine residue and a leucine residue. Examples of the "hydrophilic neutral amino acid residue" include a serine residue, a threonine residue, an asparagine residue and a glutamine residue. Examples of the "hydrophobic aliphatic amino acid residue" include a glycine residue and an alanine residue. Examples of the "acidic amino acid residue" include an aspartic acid residue and a glutamic acid residue. Examples of the "hydrophobic aromatic amino acid residue" a include phenylalanine residue, a tyrosine residue and a tryptophan residue. Examples of the "basic amino acid residue" include a lysine residue, an arginine residue and a histidine residue.

In a specific aspect of the present invention, for example, a DNA polymerase having a reverse transcriptase activity and comprising the sequence consisting of 12 amino acids A1-A12 in which A1 is leucine, A3 is glutamine, A5 is leucine, A7 is isoleucine, A11 is glutamic acid and A12 is alanine can be used as a material for the mutant.

A preferred example of the mutant of the present invention is a mutant of a DNA polymerase comprising the sequences consisting of 12 amino acids A1-A12 and having a reverse transcriptase activity, wherein in the mutant, the amino acid of A3 and/or A10 is replaced by an amino acid selected from the group consisting of lysine, arginine and histidine, preferably by arginine.

A more preferred example of the mutant of the present invention is a mutant of a DNA polymerase wherein the DNA polymerase has a reverse transcriptase activity and comprises a sequence consisting of 12 amino acids A1-A12:

A1 is leucine,

A2 is serine or alanine,

A3 is glutamine,

A4 is glutamic acid or asparagine,

A5 is leucine,

A6 is alanine or asparagine,

A7 is isoleucine,

A8 is proline, serine or threonine,

A9 is tyrosine, arginine or glutamine,

A10 is glutamic acid or lysine,

A11 is glutamic acid, and

A12 is alanine;

and in the mutant, A3 and/or A10 is replaced by a basic amino acid residue that is different from the amino acid residue before introduction of mutation, for example, by an amino acid selected from the group consisting of lysine, arginine and histidine.

For example, in the case of a DNA polymerase having a reverse transcriptase activity from *Thermus thermophilus*, an amino acid sequence from positions 680 to 691 in SEQ ID NO: 1, specifically an amino acid sequence of "LSQELAIPYEEA" (SEQ ID NO: 18) corresponds to the sequence consisting of A1 to A12. Thus, an example of the mutant of the present invention is a mutant of the DNA polymerase from *Thermus thermophilus* in which the glutamine residue at A3 (position 682) and/or the glutamic acid residue at A10 (position 689) is replaced by an amino acid selected from the group consisting of lysine, arginine and histidine, preferably arginine. A *Thermus thermophilus*-derived DNA polymerase mutant having "LSRELAIPYREA" (SEQ ID NO: 19) can be preferably used as a DNA polymerase mutant suitable for a reverse transcriptase reaction and a nucleic acid amplification reaction. For example, mutant b13b46 which is a mutant of a DNA polymerase from *Thermus thermophilus* prepared in Example 1 has mutations Q682R and E689R as described above.

Similar mutants can be also prepared from DNA polymerases having a reverse transcriptase activity from *Ther-*

*mus aquaticus, Bacillus cardotenax, Bacillus stearothermophilus*, and *Alicyclobacillus acidocaldarius*.

In a specific aspect of the present invention, for example, a DNA polymerase having a reverse transcriptase activity from *Bacillus* cardotenax has the sequence of "LAONLNIS-RKEA" (SEQ ID NO: 20) as the sequence consisting of 12 amino acids A1-A12. Similarly, the 12-amino acid sequence of a DNA polymerase having a reverse transcriptase activity from *Bacillus stearothermophilus* is the sequence of "LAONLNITRKEA" (SEQ ID NO: 21). Furthermore, the 12-amino acid sequence of a DNA polymerase having a reverse transcriptase activity from *Alicyclobacillus acidocaldarius* is the sequence of "LAQNLNIPQKEA" (SEQ ID NO: 22). The 12-amino acid sequence of a DNA polymerase having a reverse transcriptase activity from *Thermus aquaticus* is the sequence of "LSQELAIPYEEA" (positions 678 to 689 of SEQ ID NO: 25). When A3 and/or A10 in these amino acid sequences is replaced by a basic amino acid residue, the resulting mutants are cited as examples of the mutant of the present invention. In the mutants, for example, A3 and/or A10 is replaced by an amino acid selected from the group consisting of lysine, arginine and histidine. Particularly preferred is a mutant in which A3 and/or A10 is replaced by arginine. In addition to these mutants, examples of the DNA polymerase mutant of the present invention include mutants obtained by introducing the same mutation(s) as described above into heat-resistant polymerases from thermophilic bacteria and mesophilic DNA polymerases suitable for isothermal nucleic acid amplification methods. In other words, Pol I type or family A type DNA polymerases can also be suitably used as a target for introduction of mutation in the present invention.

The DNA polymerase mutant of the present invention may comprise the above-described mutation(s) in combination with a mutation introduced into a position other than the 12 amino acid sequence of A1-A12, as long as the reverse transcriptase activity and the nucleic acid amplification activity are not impaired. Examples of such a DNA polymerase mutant include, but not limited to, functional DNA polymerases having an amino acid sequence identity of at least 80%, 818, 828, 83%, 84%, 85%, 86%, 87%, 88%, 89%, 90%, 91%, 92%, 93%, 94%, 95%, 96%, 97%, 98% or 99% in a portion other than the 12 amino acid sequence of A1-A12 to the amino acid sequence of a DNA polymerase having a reverse transcriptase activity before introduction of mutation, for example a DNA polymerase having a reverse transcriptase activity from *Thermus thermophilus* (NCBI Reference Sequence WP 0112288405.1) or a DNA polymerase having a reverse transcriptase activity from *Thermus aquaticus* (Genbank Acc. No. BAA06775.1). These DNA polymerases can be suitably used in RT-PCR. Similarly, for RT-isothermal nucleic acid amplification, examples of the DNA polymerase mutant include functional DNA polymerases having an amino acid sequence identity of at least 80%, 81%, 82%, 83%, 84%, 85%, 86%, 87%, 88%, 89%, 90%, 91%, 92%, 93%, 94%, 95%, 96%, 97%, 98% or 99% in a portion other than the 12 amino acid sequence of A1-A12 to the amino acid sequence of a DNA polymerase having a reverse transcriptase activity from *Bacillus* cardotenax (NCBI Reference Sequence WP 0475858145.1), a DNA polymerase having a reverse transcriptase activity from *Bacillus stearothermophilus* (Genbank Acc. No. AAA8558.1) (SEQ ID NO: 28) or a DNA polymerase having a reverse transcriptase activity from *Alicyclobacillus acidocaldarius* (Genbank Acc. No. BAF3333.1).

The DNA polymerase mutant having a reverse transcriptase activity of the present invention may be a mutant further lacking an exonuclease activity. For example, regarding DNA polymerases from *Thermus thermophilus, Thermus aquaticus, Bacillus cardotenax, Bacillus stearothermophilus, Alicyclobacillus acidocaldarius* etc., there are known mutants lacking a 5→3 exonuclease activity. The mutants lacking the exonuclease activity lack a 5→3 exonuclease domain located at the N-terminal sides of the DNA polymerases. The mutant of the present invention may be a mutant having no 5→3 exonuclease activity in which the 5→3 exonuclease domain is deleted.

Use of the DNA polymerase mutant having a reverse transcriptase activity of the present invention results in production of a desired cDNA even under reverse transcription reaction conditions under which the DNA polymerase before introduction of mutation cannot achieve reverse transcription. Examples of the reverse transcription reaction conditions include reduced reaction time, and elevated reaction temperature. Further, use of the DNA polymerase mutant having a reverse transcriptase activity of the present invention results in an increased amount of a reverse transcription reaction product as compared to use of the DNA polymerase before introduction of mutation when reverse transcription is performed under the same conditions. For example, a reverse transcription reaction using a DNA polymerase having a reverse transcriptase activity from *Thermus thermophilus* requires a reaction time of about 30 minutes at 60° C. When the mutant of the present invention prepared from the DNA polymerase having a reverse transcriptase activity from *Thermus thermophilus* is used, the reverse transcription reaction at 60° C. can be completed in a short time of 1 to 5 minutes. In addition, the mutant of the present invention is superior in a reverse transcription reaction to a DNA polymerase mutant having a reverse transcriptase activity prepared by a technique disclosed in Japanese Patent No. 3844975. The mutant of the present invention is expected to have further improvements in terms of resistance to inhibitors during reaction and affinity with nucleic acid templates as compared to conventional DNA polymerases having a reverse transcriptase activity. According to the present invention, the reverse transcriptase activity of Pol I type or family A type DNA polymerases which originally have a low reverse transcriptase activity can be remarkably improved, and thus a DNA polymerase mutant having a reverse transcriptase activity suitable for performing a reverse transcription reaction and a nucleic acid amplification reaction can be created.

The mutant of the present invention may be a fusion protein with a PIP box (PCNA interaction protein box). PCNA, which is a protein that promotes a DNA polymerase activity, can also promote the reverse transcriptase activity of a DNA polymerase having a reverse transcriptase activity. The DNA polymerase mutant of the present invention fused with a PIP box can be prepared, for example, by using a combination of a technique as described herein and a technique as described in WO2017/090685.

2. Composition or Kit Containing the DNA Polymerase Mutant of the Present Invention The composition of the present invention means a composition comprising the DNA polymerase mutant having a reverse transcriptase activity of the present invention as described above. As an aspect of the composition of the present invention, provided is a composition suitable for a reverse transcription reaction and a nucleic acid amplification reaction which comprises the DNA polymerase mutant suitable for a reverse transcriptase reaction and a nucleic acid amplification reaction of the present invention as described in above section 1 and other components, for example components necessary for a reverse transcription reaction and a polymerase chain reaction (RT-PCR), such as a divalent metal salt, dNTPs, a buffer component, a reducing agent, sterilized water, etc. The composition of the present invention may also comprise an appropriate primer when an RNA to be amplified/detected is known. When the mutant of the present invention is suitable for a reverse transcription reaction and an isothermal nucleic acid amplification reaction, the composition of the present invention preferably comprises the same components as described above as long as the composition comprises components necessary for a reverse transcription reaction and an isothermal nucleic acid amplification reaction.

Examples of a divalent metal ion constituting the divalent metal salt include, but not limited to, a manganese ion and a magnesium ion. The divalent metal ions and their concentration suitable for reverse transcriptase are known in the art. The divalent metal ions may be supplied in the form of a salt such as chloride, sulfate or acetate. For example, the concentration of the divalent metal ion in the composition of the present invention may be preferably 0.5 to 20 mM. As the dNTP, at least one selected from the group consisting of dATP, dCTP, dGTP and dTTP, and their derivatives is used. Preferably, a mixture of dATP, dCTP, dGTP and dTTP is used.

Examples of the buffer component for maintaining pH include, but not limited to, a Tris buffer, a tricine buffer, a bicine buffer, a HEPES buffer, an acetate buffer, and a phosphate buffer. For example, the buffer components and their concentration suitable for a reverse transcription reaction and a nucleic acid amplification reaction are known in the art. Examples of the reducing agent for a reverse transcription reaction include, but not limited to, DTT (dithiothreitol) and 2-mercaptoethanol. The reducing agents and their concentration suitable for a reverse transcription reaction are known in the art.

For a reverse transcription reaction, for example, a random 6-mers oligo dT primer, and a gene-specific primer can be used as a primer. The chain length of the primer is preferably 6 nucleotides or more, more preferably 10 nucleotides or more from the viewpoint of hybridization specificity, and preferably 100 nucleotides or less, more preferably 30 nucleotides or less from the viewpoint of oligonucleotide synthesis. As a random primer for non-synthesis, a mixture of oligonucleotides specific cDNA having chain length of 6 to 8 nucleotides may be used. The oligonucleotide may be chemically synthesized, for example, by a known method, or may be derived from a biological sample. The oligonucleotide derived from a biological sample may be prepared, for example, by digesting a DNA prepared from a natural sample with a restriction endonuclease and then isolating the oligonucleotides from the digested product. For a nucleic acid amplification reaction, the composition of the present invention may comprise a pair of primers designed for a nucleic acid sequence to be amplified. The primer for a reverse transcription reaction may also serve as one of the pair of primers for a nucleic acid amplification.

The kit of the present invention is a kit for RT-PCR or a kit for RT-isothermal nucleic acid amplification which is suitable for a reverse transcription reaction method and a nucleic acid amplification reaction method. The kit of the present invention contains the DNA polymerase mutant suitable for a reverse transcription reaction and a nucleic acid amplification reaction of the present invention as described in above section 1, and a divalent metal salt, dNTPs, a buffer component, a reducing agent, or other components suitable for a reverse transcription reaction and a nucleic acid amplification reaction. Examples of the kit of the present invention include a kit for preparing a reverse transcription reaction/nucleic acid amplification reaction solution by mixing the components contained in the kit when used, a kit containing the composition of the present invention as described above which can be used only by adding a DNA template and water (sterile water etc.) to the composition when used, and a kit containing the composition of the present invention as described above in a dry form. A kit for detecting a specific RNA which contains primers specific for the target RNA and an RNA as a positive control is also included in the present invention. The divalent metal salt, the dNTPs, the buffer component and the reducing agent are as described above.

The composition and kit of the present invention may further contain a component necessary for detecting an amplified double-stranded nucleic acid, for example an intercalator or a fluorescently labeled probe. Examples of the intercalator include SYBR (registered trademark), Green I, TB Green (registered trademark), and other nucleic acid-binding dyes. Examples of the fluorescently labeled probe include TaqMan (registered trademark) probes, Cycleave (registered trademark) probes, and molecular beacon probes.

3. Method for Producing DNA Polymerase Mutant Having Reverse Transcriptase Activity of the Present Invention The method for producing a DNA polymerase mutant suitable for a reverse transcriptase reaction and a nucleic acid amplification reaction of the present invention relates to a method for producing the DNA polymerase mutant as described in above section 1.

A specific aspect of the production method of the present invention is a method for producing a DNA polymerase having a reverse transcriptase activity suitable for nucleic acid amplification from an RNA, the method comprising:

(1) a step of selecting a DNA polymerase comprising a sequence consisting of 12 amino acids A1-A12:
A1 is a branched chain amino acid residue,
A2 is a hydrophilic neutral amino acid residue or a hydrophobic aliphatic amino acid residue,
A3 is a hydrophilic neutral amino acid residue,
A4 is an acidic amino acid residue or a hydrophilic neutral amino acid residue,
A5 is a branched chain amino acid residue,
A6 is a hydrophobic aliphatic amino acid residue or a hydrophilic neutral amino acid residue,
A7 is a branched chain amino acid residue,
A8 is a proline residue or a hydrophilic neutral amino acid residue,
A9 is a hydrophobic aromatic amino acid residue, a basic amino acid residue, or a hydrophilic neutral amino acid residue,
A10 is an acidic amino acid residue or a basic amino acid residue,
A11 is an acidic amino acid residue, and
A12 is a hydrophobic aliphatic amino acid residue; and (2) a step of replacing A3 and/or A10 in the sequence consisting of 12 amino acids of the DNA polymerase selected in step (1) by a basic amino acid residue that is different from the amino acid residue before introduction of mutation.

In the above aspect, a DNA polymerase comprising the sequence consisting of 12 amino acids in which A1 is leucine, A3 is glutamine, A5 is leucine, A7 is isoleucine, A11 is glutamic acid and A12 is alanine may be selected as a material for introduction of mutation.

In step (2) of the production method of the present invention, A3 and/or A10 in the selected DNA polymerase having a reverse transcriptase activity is preferably replaced by is an amino acid selected from the group consisting of lysine, arginine and histidine, more preferably by arginine.

Step (1) can be performed by extracting a DNA polymerase comprising the sequence consisting of 12 amino acids A1-A12 by a conventional method, for example by computer homology search. For the search, known amino acid sequence database can be used.

Step (2) is performed by preparing a nucleic acid encoding the DNA polymerase selected in step (1), and converting codons corresponding to A3 and/or A10 in the nucleic acid into codons of basic amino acid residues. Such base substitution can be performed by a known method. For example, a commercially available kit for introduction of mutation may be used. The full length of a nucleic acid encoding the mutant into which the mutation(s) is introduced may be chemically synthesized. Furthermore, the introduction of mutation as described above may be combined with introduction of mutation into a position other than the 12 amino acid sequence of A1-A12.

For producing the DNA polymerase mutant having a reverse transcriptase activity of the present invention, a nucleic acid encoding the mutant can be prepared and introduced into an appropriate host to express the mutant. Codon optimization may be performed to allow the expression of the mutant of interest in the host used or to increase the expression level. The codon optimization is preferably performed by a method commonly used in the art.

In the production of the DNA polymerase mutant having a reverse transcriptase activity of the present invention, a nucleic acid encoding the amino acid sequence of the mutant can be inserted into an appropriate expression vector to produce the mutant. The expression vector preferably contains a nucleic acid encoding the mutant of the present invention and an expression regulatory sequence operably linked to the nucleic acid. Examples of the expression regulatory sequence include, but not limited to, a promoter, a gene involved in regulation of a promoter, a ribosome binding sequence, a polyadenylation signal, a transcription termination sequence (transcription terminator), and an enhancer. The expression vector may further contain a gene encoding a marker (drug resistance gene, fluorescence marker, luminescence marker, etc.) used for selection of a transformant.

As the expression vector into which a nucleic acid encoding the DNA polymerase mutant having a reverse transcriptase activity of the present invention is inserted, any expression vector commonly used in the art can be used. Examples of the expression vector include, but not limited to, a vector capable of self-replicating in a host cell, and a vector capable of being integrated into a host chromosome. A vector compatible with the host may be used.

Examples of the expression vector into which a nucleic acid encoding the DNA polymerase mutant having a reverse transcriptase activity of the present invention is inserted include a plasmid vector, a phage vector, and a viral vector. As the plasmid vector, a plasmid suitable for the host used can be used. For example, a plasmid derived from *Escherichia coli*, a plasmid derived from a bacterium of the genus *Bacillus*, and a plasmid derived from yeast are well known to those skilled in the art, and there are many commercially available plasmids. Such known plasmids and their mutants can be used in the present invention. As the phage vector, for example, λ phage (for example, Charon4A, Charon21A, EMBL3, EMBL4, λgt10, λgt11, λZAP) can be used. As the viral vector, for example, an animal virus such as a retrovirus or a vaccinia virus, or an insect virus such as a baculovirus can be used. Furthermore, many heterologous protein expression systems using yeast, insect cells, and mammalian cells as hosts have been constructed, and already commercially available. These expression systems may be used for the production of the DNA polymerase mutant having a reverse transcriptase activity of the present invention.

The promoter to be loaded with the expression vector used in the production method of the present invention can be selected depending on the host. When the host is *Escherichia coli*, examples of the promoter include, but not limited to, promoters derived from *Escherichia coli* and phage, such as trp promoter, lac promoter, PL promoter, and PR promoter, and their modifications. Furthermore, an expression system (for example, a pET expression system, etc.) containing a combination of a phage-derived promoter and an RNA polymerase gene may be used.

In order to facilitate purification of an expressed polypeptide, the expression vector of the present invention may further contain a nucleic acid encoding an affinity tag. A nucleic acid encoding the affinity tag is inserted into the vector so that a fusion protein of the reverse transcriptase mutant of the present invention with the affinity tag is expressed. Examples of the affinity tag include, but not limited to, a histidine (His) tag, a glutathione S-transferase (GST) tag, a maltose binding protein (MBP) tag, and a Strep (II) tag consisting of 8 amino acid residues (Trp-Ser-His-Pro-Gln-Phe-Glu-Lys). The tag may be added to the 5'-end and/or the 3'-end side of a nucleic acid encoding the DNA polymerase mutant having a reverse transcriptase activity of the present invention. The tag may be appropriately added to a position that does not interfere with expression and tag function. It is preferable that the tag can be cleaved at a purification stage of the expressed polypeptide. Examples of such a tag capable of being cleaved include, but not limited to, tags containing nucleic acids encoding the recognition sequences of proteases for cleavage of fusion polypeptides such as Factor Xa, Prescision Protease, Thrombin, enterokinase, and TEV protease (Tobacco Etch Virus protease).

4. Method for Improving DNA Polymerase Having Reverse Transcriptase Activity of the Present Invention The method for improving a DNA polymerase having a reverse transcriptase activity of the present invention can be performed as described below. The method comprises in a DNA polymerase having a reverse transcriptase activity comprising a sequence consisting of 12 amino acids A1-A12, replacing the amino acid A3 and/or A10 by another basic amino acid residue.

In the improvement method of the present invention, first, a DNA polymerase having a reverse transcriptase activity comprising a sequence consisting of 12 amino acids A1-A12 as shown below can be selected as a candidate for a DNA polymerase before introduction of mutation.

A1 is a branched chain amino acid residue;
A2 is a hydrophilic neutral amino acid residue or a hydrophobic aliphatic amino acid residue;
A3 is a hydrophilic neutral amino acid residue;
A4 is an acidic amino acid residue or a hydrophilic neutral amino acid residue;
A5 is a branched chain amino acid residue;
A6 is a hydrophobic aliphatic amino acid residue or a hydrophilic neutral amino acid residue;
A7 is a branched chain amino acid residue;
A8 is a proline residue or a hydrophilic neutral amino acid residue;

A9 is a hydrophobic aromatic amino acid residue, a basic amino acid residue, or a hydrophilic neutral amino acid residue;

A10 is an acidic amino acid residue or a basic amino acid residue;

A11 is an acidic amino acid residue; and

A12 is a hydrophobic aliphatic amino acid residue.

An example of a method for selecting a DNA polymerase having a reverse transcriptase activity as a candidate comprises extracting a DNA polymerase comprising the amino acid sequence consisting of A1-A12 by a conventional method, for example, by computer homology search. The search can be performed using known amino acid sequence databases.

In a specific aspect of the present invention, a DNA polymerase comprising the sequence consisting of 12 amino acids in which A1 is leucine, A3 is glutamine, A5 is leucine, A7 is isoleucine, A11 is glutamic acid and A12 is alanine is preferably used as a material for introduction of mutation. In the DNA polymerase having a reverse transcriptase activity thus selected, the amino acid A3 and/or A10 is replaced by another basic amino acid residue, and thereby the improvement of the DNA polymerase is attained. Specifically, the reverse transcription activity of the DNA polymerase is enhanced, and the production amount of a reverse transcription product (CDNA) per reaction time is increased.

For the amino acid replacement as described above, it is preferable that A3 and/or A10 is replaced by an amino acid selected from the group consisting of lysine, arginine and histidine. Particularly preferred is the replacement by an arginine residue. In the improvement method of the present invention, a further mutation may be introduced into a position other than the 12 amino acid sequences of A1-A12 as long as the reverse transcriptase activity and nucleic acid amplification activity are not impaired. In the present invention, examples of the DNA polymerase having a reverse transcriptase activity to be improved include, but not limited to, DNA polymerases from *Thermus thermophilus, Thermus aquaticus, Bacillus cardotenax, Bacillus stearothermophilus*, and *Alicyclobacillus acidocaldarius*, heat-resistant polymerases from thermophilic bacteria, mesophilic DNA polymerases suitable for isothermal nucleic acid amplification methods, and altered polymerases from the above-described polymerases by amino acid replacement, insertion or deletion, and other altered polymerases derived from the above-described polymerases. In other words, the DNA polymerase having a reverse transcriptase activity to be improved may be a Pol I type or family A type DNA polymerase which originally has a low reverse transcriptase activity.

EXAMPLE

Hereinafter, the present invention will be explained in detail by means of Examples to which the scope of the present invention is not limited.

Experimental Method:

(1) Method for Preparing Tth DNA Polymerase Mutant

A nucleotide sequence of a gene encoding wild-type DNA polymerase from *Thermus thermophilus* (Tth) HB8 strain is published under NCBI Reference Sequence No. WP 011228405.1. An amino acid sequence of the DNA polymerase is shown in SEQ ID NO: 1. Artificial genes having sequences comprising mutations introduced into specific positions (a partial sequence consisting of 12 amino acids A1-A12) in the amino acid sequence were chemically synthesized. The artificial genes thus obtained were introduced into plasmid pET6xHN-N (manufactured by Takara Bio USA) using In-Fusion (registered trademark) HD Cloning Kit (manufactured by Takara Bio USA). The plasmids thus obtained had nucleotide sequences encoding Tth DNA polymerase mutants having histidine tags at the N-terminal sides.

Next, *Escherichia coli* BL21 DE3 strain (manufactured by Takara Bio Inc.) was transformed with the plasmid and cultured overnight at 37° C. on a 1.5% agarose LB plate containing 100 µg/mL ampicillin. Three single colonies were selected from the plate. The single colony was inoculated into an LB medium containing 100 µg/mL ampicillin (hereinafter referred to as an LB-AP medium), and cultured with shaking overnight at 37° C. Then, 300 µL of the culture solution was inoculated into 25 mL of an LB-AP medium and cultured with shaking overnight at 37° C. When an OD600 value of 0.6 was reached, IPTG was added at a final concentration of 1 mM to the culture solution. After culturing for induction at 37° C. for 21 hours, bacterial cells were collected.

The bacterial cells thus obtained were suspended in a solution containing 2 mL of 50 mM Tris HCl pH 8.0 (4° C.), 100 mM NaCl, 1 mM EDTA (pH 8.0) and 5% glycerol (hereinafter referred to as Buffer S). Lysozyme (manufactured by Sinopharm Chemical Reagent Co., Ltd.) was added at a final concentration of 0.1 mg/mL to the suspension. After shaking at 4° C. for 1 hour, a mixture was centrifuged at 15,000× g for 30 minutes at 4° C. A supernatant was collected. The supernatant collected was kept at 85° C. for 15 minutes and then centrifuged at 15,000× g for 30 minutes at 4° C. The supernatant after heating was concentrated about 20-fold by centrifugation using an Amicon Ultra-0.5 mL column.

The concentrate thus obtained was used as a Tth DNA polymerase mutant crude solution in experiments as described below. Regarding DNA polymerase activity, the number of units of the enzyme used was calculated on the basis of the activity of incorporating 10 nmol of all nucleotides into an acid-insoluble precipitate in a reaction solution at pH 9.3 for 30 minutes at 74° C. using an activated salmon sperm DNA as a template/primer, which is regarded as 1 U.

(2) Method for Evaluating Reverse Transcription Activity of Tth DNA Polymerase Mutants The Tth DNA polymerase mutants obtained in (1) were tested for reverse transcription reaction by the following method. For the Tth DNA polymerase mutant crude extraction solution, a reaction solution in an final volume of 50 µL was prepared, and the reaction solution contained 5 X RT-PCR buffer [bicine buffer (pH 8.2) at a final concentration of 50 mM, potassium acetate at a final concentration of 115 mM, glycerol at a final concentration of 8%], manganese acetate at a final concentration of 2.5 mM, BSA at a final concentration of 0.1%, a pair of primers having nucleotide sequences shown in SEQ ID NOS: 2 and 3 at a final concentration of 0.2 µM, a probe having a nucleotide sequence shown in SEQ ID NO: 4 at a final concentration of 0.2 µM, dNTP at a final concentration of 0.3 mM, an RNA template having chain length of 4.4 kb [an RNA corresponding to a region from nucleic acid numbers 12697 to 17090 of λDNA (GenBank ACC. No. J0245.9.1), corresponding to $1\times10^7$ copies], 5 U of the Tth DNA polymerase mutant prepared in Experimental method (1), and 2.5 U of Taq antibody (manufactured by Takara Bio Inc.). As a control, a reaction solution containing the wild-type Tth DNA polymerase was also prepared.

RT-PCR conditions comprised treatment at 90° C. for 30 seconds, at 60° C. for 1 minute and then at 95° C. for 1 minute, and then 45 cycles in which 1 cycle comprised 95° C. for 15 seconds and 56° C. for 45 seconds. Real-time PCR was performed using TP-990 Thermal Cycler Dice (registered trademark) Real Time System III (manufactured by Takara Bio Inc.) as a thermal cycler, and a Ct value was measured.

Example 1: Preparation of Tth DNA Polymerase Mutant

According to Experimental method (1), an artificial gene encoding a mutant protein in which glutamine at position 682 in the wild-type amino acid sequence of Tth DNA polymerase was replaced by arginine was prepared. A recombinant plasmid carrying the obtained artificial gene was prepared. According to Experimental method (1), the protein was expressed, and the expressed protein was purified. A Tth DNA polymerase mutant thus obtained had a replacement mutation from glutamine to arginine at position 682 (Q682R), which was named "b13". Similarly, a Tth DNA polymerase mutant in which glutamic acid at position 689 in the wild-type amino acid sequence of Tth DNA polymerase was replaced by arginine (E689R) (which was named "b46"), and a Tth DNA polymerase mutant in which glutamine at position 682 was replaced by arginine and glutamic acid at position 689 was replaced by arginine (Q682R+E689R) (which was named "b13b46") were prepared. The amino acid sequences and nucleic acid sequences of the mutant proteins are shown in SEQ ID NOs: 5-10.

Example 2: Reverse Transcription Activity Evaluation Test of Tth DNA Polymerase Mutant-1

The Tth DNA polymerase mutants prepared in Example 1 and the wild-type Tth DNA polymerase were evaluated for reverse transcription activity according to Experimental method (2). When the wild-type Tth DNA polymerase is commonly used, the standard reverse transcription reaction is performed at 60° C. for 30 minutes. In this example, the performance of the enzymes was compared in a short time of reverse transcription reaction at 60° C. for 1 minute. Results are shown in Table 1. Since a Ct value is inversely proportional to the starting amount of a target, the Ct value can be used to calculate the starting copy number of a DNA. For example, if the Ct value is smaller by 1 (minus 1), the amount of a DNA that can be used as a template in PCR is doubled.

TABLE 1

| | RT-PCR Ct value | |
|---|---|---|
| Mutation type | ΔCt | Conversion to starting amount of DNA template in PCR |
| No mutation, wild-type | Standard value, (0) | 1 |
| b46 | −7.2 | 146 |
| b13 | −8.5 | 360 |
| b13b46 | −10.3 | 1287 |

As shown in Table 1, the starting DNA template amounts in PCR when mutants b13, b46 and b13b46 were used were 100 to 1000 or more times the starting DNA template amount in PCR when the wild-type enzyme was used. The increase in the DNA template amount means that the amount of cDNA produced by a reverse transcription reaction before PCR increased. Thus, it was found that the mutants had a 100 to 1000 or more times higher activity in the reverse transcription reaction than the wild-type enzyme.

Example 3: Fusion Protein of PIP Box and Tth Mutant

Fusion proteins of the Tth DNA polymerase mutants described in Example 1 and a PCNA binding domain were studied. First, a fusion protein of 3 PIPs and the wild-type Tth DNA polymerase (PIP-L14-PIP-L14-PIP-L15-Tth DNA polymerase) having the amino acid sequence shown in SEQ ID NO: 11 in which the 3 PIPs comprised three PIP boxes arranged in tandem and were fused to the N-terminal side of each Tth DNA polymerase mutant was prepared according to a method as described in Example 4 of WO2017/090685. The fusion protein was named "3PIP-wild type". Similarly, fusion proteins of 3PIP with mutants b13, b46 and b13b46 described in Example 1 were prepared, and named "3PIP-b13", "3PIP-b46" and "3PIP-b13b46". In addition, a Puf PCNA D143R mutant (PCNA13), which is a polymerase-related factor that recognizes the PIP box, was prepared by a method as described in Examples of WO2007/004654.

In this Example, an RNA used as a template for the reverse transcription reaction was prepared as described below. RNAs having nucleotide sequences comprising regions that are amplified by PCR using primers for GI detection and for GII detection having the same nucleotide sequences as described in "The detection method of norovirus" (Appendix attached to Notice No. 1105001 dated on Nov. 5, 2003; final revision: 1022-No. 1 dated on Oct. 22, 2013) published by the Inspection and Safety Division, Food Safety Department, Pharmaceutical and Food Safety Bureau, Ministry of Health, Labor and Welfare (hereinafter referred to as "the official method") were prepared by a conventional method.

A reaction solution containing the RNA template prepared by the above-described method and 5 X RT-PCR buffer, manganese acetate at a final concentration of 2.5 mM, BSA at a final concentration of 0.1%, the GI primer pair having nucleotide sequences shown in SEQ ID NOs: 12 and 13 as defined by the official method at a final concentration of 0.2 μM or the GII primer pair having nucleotide sequences shown in SEQ ID NOS: 14 and 15 as defined by the official method at a final concentration of 0.2 μM, a probe for GI detection having a nucleotide sequence shown in SEQ ID NO: 16 at a final concentration of 0.2 μM or a probe for GII detection having a nucleotide sequence shown in SEQ ID NO: 17 at a final concentration of 0.2 μM, dNTP at a final concentration of 0.3 mM, poly(ethylene glycol) 4-nonylphenyl 3-sulfopropyl ether at a final concentration of 48, PCNA13 at a final concentration of 850 nM, and 5 U of the above-described 3PIP-Tth DNA polymerase mutant was prepared in a final volume of 25 μL. As controls, a reaction solution containing the wild-type Tth DNA polymerase and a reaction solution containing the wild-type Tth DNA polymerase with the 3PIPs added to the N-terminal side were also prepared. RT-PCR conditions comprised treatment at 58° C. for 5 minutes and 95° C. for 30 seconds, then reaction of 5 cycles in which 1 cycle comprised 95° C. for 5 seconds and 56° C. for 1 minute, and subsequently reaction of 40 cycles in which 1 cycle comprised 90° C. for 5 seconds and 56° C. for 1 minute. The 5 same thermal cycler as used in Example 2 was used. Results of GI detection are shown in Table 2. Similarly, results of GII detection are shown in Table 3.

TABLE 2

| Mutation type | RT-PCR Ct value ΔCt | Conversion to starting amount of DNA template in PCR |
|---|---|---|
| Wild-type (without PIP) | Standard value, (0) | 1 |
| 3PIP-wild type | −7.0 | 124 |
| 3PIP-b13 | −9.4 | 676 |
| 3PIP-b46 | −9.8 | 873 |
| 3PIP-b13b46 | −10.7 | 1698 |

TABLE 3

| Mutation type | RT-PCR Ct value ΔCt | Conversion to starting amount of DNA template in PCR |
|---|---|---|
| Wild-type | Standard value, (0) | 1 |
| 3PIP-wild type | −7.8 | 223 |
| 3PIP-b13 | −9.9 | 923 |
| 3PIP-b46 | −10.7 | 1710 |
| 3PIP-b13b46 | −12.3 | 4871 |

As shown in Tables 2 and 3, the starting DNA template amounts increased when mutants b13, b46 and b13b46 of the present invention with the PIP boxes added to the N-terminal sides were used, as compared to when the wild-type enzyme and the wild-type enzyme with the PIP boxes added to the N-terminal side were used.

Example 4: Reverse Transcription Activity Evaluation Test of Tth DNA Polymerase Mutant—2

The mutants b13 and b13b46 whose activity in the reverse transcription reaction was found to be enhanced in Example 2 were evaluated for detection of norovirus in an actual sample. A norovirus-positive stool sample was obtained from a subject who gave informed consent, suspended in PBS at about 10% (w/v), and then centrifuged at 15,000 rpm for 5 minutes. A supernatant (1 μL) thus obtained was used in a reaction as described below. A reaction solution containing 1 μL of the stool supernatant, 5 X RT-PCR buffer [tricine buffer (pH 8.15) at a final concentration of 50 mM, potassium acetate at a final concentration of 50 mM, glycerol at a final concentration of 88, DMSO at a final concentration of 1%, manganese acetate at a final concentration of 2.5 mM, BSA at a final concentration of 0.1%], the GI primer pair as defined by the official method at a final concentration of 0.2 μM, a probe for GI detection at a final concentration of 0.2 μM, dNTP at a final concentration of 0.3 mM, 5 U of the above-described 3PIP-Tth DNA polymerase mutant, poly(ethylene glycol) 4-nonylphenyl 3-sulfopropyl ether at a final concentration of 4%, and 2.5 U of Taq antibody (manufactured by Takara Bio Co., Ltd.) was prepared in a final volume of 25 μL. As a control, a reaction solution containing the wild-type Tth DNA polymerase was also prepared. In the case of using Tth DNA polymerase, RT-PCR conditions comprised treatment at 90° C. for 3 minutes, 58° C. for 5 minutes or 30 minutes, and 95° C. for 30 seconds, then reaction of 5 cycles in which 1 cycle comprised 95° C. for 5 seconds and 56° C. for 30 seconds, and subsequently reaction of 40 cycles in which 1 cycle comprised 90° C. for 5 seconds and 56° C. for 30 seconds. In the case of using Tth DNA polymerase mutants, RT-PCR conditions comprised treatment at 90° C. for 3 minutes, 58° C. for 5 minutes and 95° C. for 30 seconds, then reaction of 5 cycles in which 1 cycle comprised 95° C. for 5 seconds and 56° C. for 30 seconds, and subsequently reaction of 40 cycles in which 1 cycle comprised 90° C. for 5 seconds and 56° C. for 30 seconds. The same thermal cycler as used in Example 2 was used.

As a result of the above experiments, norovirus GI in stools was detected using the Tth DNA polymerase only when the reverse transcription reaction was performed 58° C. for 30 minutes. On the other hand, norovirus GI in stools was detected using the mutants b13 and b13b46 of the present invention even when the reverse transcription reaction was performed at 58° C. for a short period of 5 minutes. These results show that the mutants of the present invention retain the enhanced activity in the reverse transcriptase reaction even when they are used for detection in actual samples.

Example 5: Reverse Transcription Activity Evaluation Test of Tth DNA Polymerase Mutant—3

The Tth DNA polymerase mutants of the present invention were compared to Tth DNA polymerase mutants that were previously reported to enable a high-temperature and efficient reverse transcription reaction. Crude enzyme solutions of the Tth DNA polymerase mutants were prepared by Experimental method (1), according to Japanese Patent No. 3844975. Specifically, since position 681 in the amino acid sequence of Taq DNA polymerase (Genbank Acc. No. BAA06775.1) corresponds to position 683 in the amino acid sequence of Tth DNA polymerase based on the amino acid sequence described in NCBI Reference Sequence No. WP 0112288405, glutamic acid at position 683 in the amino acid sequence was replaced by phenylalanine, lysine, leucine, arginine or tyrosine to prepare Tth DNA polymerase mutants. These amino acid mutants were named mutants E683F, E683K, E683L, E683R, and E683Y.

The evaluation was performed by Experimental method (2) as described above, except that the reverse transcription reaction time was changed from 1 minute to 2 minutes at 60° C. Results are shown in Table 4.

TABLE 4

| Mutation type | RT-PCR Ct value ΔCt | Conversion to starting amount of DNA template in PCR |
|---|---|---|
| b13b46 | Standard value, (0) | 1 |
| E683F | | No amplification |
| E683K | +1.22 | 0.43 |
| E683L | | No amplification |
| E683R | +3.81 | 0.07 |
| E683Y | | No amplification |

As shown in Table 4, the Tth DNA polymerase mutants comprising replacement of glutamic acid at position 683 could not produce an amplified product from the template, or produced higher Ct values than the Tth DNA polymerase mutant of the present invention. The results mean that the starting DNA template amount at the start of PCR decreased, in other words, the amount of CDNA produced by the reverse transcription reaction before PCR was about ½ or less, as compared to the mutant of the present invention. Thus it was found that the mutant of the present invention is superior in the reverse transcription reaction activity to the mutants prepared by the prior art technique.

Experimental Method (3) Method for Preparing Bca DNA Polymerase Mutant

A nucleotide sequence of a gene encoding wild-type DNA polymerase from *Bacillus* caldoteneax (Bca) is published under NCBI Reference Sequence No. NZ CP02574.1. An amino acid sequence of the DNA polymerase is shown in SEQ ID NO: 23. Artificial genes having sequences comprising mutations introduced into specific positions (a partial sequence consisting of 12 amino acids A1-A12) in the amino acid sequence were chemically synthesized. According to Experimental method (1), plasmids containing the genes encoding Bac DNA polymerase mutants with histidine tags at the N-terminal sides were prepared.

Next, *Escherichia coli* BL21 DE3 strain (manufactured by Takara Bio Inc.) was transformed with the plasmid and cultured overnight at 37° C. on a 1.5% agarose LB plate containing 100 µg/mL ampicillin. Three single colonies were selected from the plate, the single colony was inoculated into an LB medium containing 100 µg/mL ampicillin (hereinafter referred to as an LB-AP medium), and cultured with shaking overnight at 37° C. Then, 30 mL of the culture solution was inoculated into 3 L of an LB-AP medium and cultured with shaking overnight at 37° C. When an OD600 value of 0.6 was reached, IPTG was added at a final concentration of 1 mM to the culture solution. After culturing for induction at 37° C. for 4 hours, bacterial cells were collected.

The bacterial cells (3g) thus obtained were suspended in 12 mL of a buffer (50 mM Tris HCl pH 7.0 (4° C.), 4 µM PMSF, 1 mM DTT, 10% glycerol), stirred with Sonic 180 W for 10 minutes, and then centrifuged at 10,000 rpm for 30 minutes at 4° C. A supernatant was collected and heated at 60° C. for 30 minutes. The supernatant after the heat treatment was cooled on ice for 30 minutes and then centrifuged at 11,000 rpm for 30 minutes (4° C.) to recover a supernatant. The supernatant thus obtained was subjected to DEAE Sepharose™ Fast Flow (matrix manufactured by GE Healthcare), CM Sephadex™ Fast Flow (matrix manufactured by GE Healthcare), Sephadex™-G100, Heparin Sepharose™ (matrix manufactured by GE Healthcare), and then Q Sepharose™ (matrix manufactured by GE Healthcare) to prepare a purified solution of Bca DNA polymerase mutant protein. The purified solution was used in tests as described below. Regarding DNA polymerase activity, the number of units of the enzyme used was calculated on the basis of the activity of incorporating 10 nmol of all nucleotides into an acid-insoluble precipitate in a reaction solution at pH 9.3 for 30 minutes at 74° C. using an activated salmon sperm DNA as a template/primer, which is regarded as 1 U.

Experimental Method (4) Method for Preparing Aac DNA Polymerase Mutant

A nucleotide sequence of a gene encoding wild-type DNA polymerase from *Alicyclobacillus acidocaldarius* (Aac) is published under NCBI Reference Sequence No. AB275481.1. An amino acid sequence of the DNA polymerase is shown in SEQ ID NO: 24. Artificial genes having sequences comprising mutations introduced into specific positions (a partial sequence consisting of 12 amino acids A1-A12) in the amino acid sequence were chemically synthesized. According to Experimental method (1), plasmids containing the genes encoding Aac DNA polymerase mutants with histidine tags at the N-terminal sides were prepared.

Next, *Escherichia coli* BL21 DE3 strain was transformed with the plasmid and cultured in the same manner as described in Experimental method (3). Thus the bacterial cells were collected.

The bacterial cells (3g) thus obtained were purified in the same manner as described in Experimental method (3) to prepare a purified solution of the Aac DNA polymerase mutant. The purified solution was used in tests as described below. The number of units of the enzyme used was calculated in the same manner as in the case of Bca DNA polymerase.

Experimental Method (5) Method for Preparing Taq DNA Polymerase Mutant

A nucleotide sequence of a gene encoding wild-type DNA polymerase from *Thermus aquaticus* (Taq) is published under NCBI Reference Sequence No. D32013.1. An amino acid sequence of the DNA polymerase is shown in SEQ ID NO: 25. Artificial genes having sequences comprising mutations introduced into specific positions (a partial sequence consisting of 12 amino acids A1-A12) in the amino acid sequence were chemically synthesized. According to Experimental method (1), plasmids containing the genes encoding Taq DNA polymerase mutants with histidine tags at the N-terminal sides were prepared.

Next, *Escherichia coli* BL21 DE3 strain was transformed with the plasmid and cultured in the same manner as described in Experimental method (3). Thus the bacterial cells were collected.

The bacterial cells (13g) thus obtained were suspended in 39 mL of a buffer [100 mM Tris HCl pH 7.5 (4° C.), 200 mM EDTA pH 7.5, 2.4 UM PMSF], stirred with Sonic 180 W for 10 minutes, and then centrifuged at 12,000 rpm for 30 minutes at 4° C. A supernatant was collected, and 1.34 g of ammonium sulfate and 0.64 mL of 10% PEI were added to the supernatant. After stirring for 30 minutes (4° C.), a mixture was centrifuged for 30 minutes (4° C.). Then, a supernatant was collected. The supernatant was heated at 75° C. for 15 minutes, cooled on ice for 30 minutes, and then centrifuged at 35,000 rpm for 60 minutes (4° C.) to recover a supernatant. The supernatant thus obtained was purified by using Phenyl Sepharose™ C1-4B (matrix manufactured by GE Healthcare). The number of units of the enzyme used was calculated in the same manner as in the case of Bca DNA polymerase.

Experimental Method (6) Method for Evaluating Reverse Transcription Activity of Bca, Aac and Taq DNA Polymerase Mutants The polymerases (Pol) activity of the Bca, Aac and Taq DNA polymerase mutants obtained in (3), (4) and (5) was measured. For the measurement of Pol activity, a reaction solution containing TAPS buffer (pH 9.3, 25° C.) at a final concentration of 25 mM, KCl at a final concentration of 50 mM, $MgCl_2$ at a final concentration of 2 mM, DTT at a final concentration of 0.1 mM, dATP, dGTP and dCTP at each final concentration of 200 µM, [3H]-dTTP at a final concentration of 100 µM, and activated salmon sperm DNA at a final concentration of 0.25 mg/ml was prepared. Specifically, activity of incorporating 10 nmol of all nucleotides into an acid-insoluble precipitate at 74° C. for 30 minutes in the reaction solution for measurement was measured using the activated salmon sperm DNA as a template/primer, and the activity measured was regarded as 1 U.

Next, the reverse transcription activity of the Bca, Aac and Taq DNA polymerase mutants obtained in (3), (4) and (5) was measured. For the measurement reverse transcription activity, a reaction solution containing 50 mM Tris-HCl pH 8.3 (37° C.), 5 mM Tris-HCl pH 7.5 (37° C.), 85 mM KCl, 8 mM MgCl$_2$, 10 mM DTT, 0.1% NP-40, 0.02 mg/ml Poly(A), 2.5 mM dTTP, and 100 µCi/ml [3H]-dTTP was prepared. Specifically, enzymatic activity of incorporating 1 nmol of [3H]-dTTP at 37° C. for 10 minutes in the reaction solution for measurement was measured using Poly(rA)·oligo (dT) 12-18 as a template/primer, and the activity measured was regarded as 1 U.

Experimental Method (7) Method for Evaluating Reverse Transcription Activity of Bca, Aac and Taq DNA Polymerase Mutants The Bca, Aac and Taq DNA polymerase mutants obtained in (3), (4) and (5) were tested for reverse transcription reaction by the following method. In this test, a part of the components of BcaBEST (trademark) RNA PCR Kit (manufactured by Takara Bio Inc.) was used. Specifically, for each DNA polymerase mutant purification solution, 2 X Bca 1st Buffer attached to the kit, 25 mM MgSO$_4$, RNase inhibitor (40 U/µl), 10 mM dNTP, a reverse transcription primer having a nucleotide sequence shown in SEQ ID NO: 26 at a final concentration of 0.5 µM, dNTP at a final concentration of 500 µM, HL60 total RNA (manufactured by Takara Bio Inc.) as a template at a final concentration of 10 ng/µL, and 0.5 µL of the purified solution of Bca, Aac or Taq DNA polymerase mutant prepared by Experimental method (3), (4) or (5) were mixed to prepare 10 µL of a reverse transcription reaction solution. As a control, a reaction solution containing wild-type Bca, Aac or Taq DNA polymerase was also prepared.

Reverse transcription conditions comprised treatment at 65° C. for 60 seconds, at 55° C. for 5 minutes, and at 95° C. for 2 minutes. As a thermal cycler, TP-990 Thermal Cycler Dice (registered trademark) Real Time System III (manufactured by Takara Bio Inc.) was used.

A cDNA solution thus obtained was subjected to real-time PCR. Real-time PCR was performed using RR420A TB Green (registered trademark) Premix Ex Taq (trademark) (Tli RNase H Plus) (manufactured by Takara Bio Inc.). A PCR reaction solution containing a forward primer having a nucleotide sequence shown in SEQ ID NO: 26 at a final concentration of 0.2 µM, a reverse primer having a nucleotide sequence shown in SEQ ID NO: 27 at a final concentration of 0.2 µM, and 1 µL of CDNA obtained by the above-described reverse transcription reaction was prepared. The PCR reaction solution (25 µL per one reaction) was subjected to real-time PCR reaction.

PCR conditions comprised initial denaturation at 90° C. for 30 seconds and then reaction of 40 cycles in which 1 cycle comprised 95° C. for 5 seconds and 60° C. for 30 seconds. Real-time PCR was performed using TP-990 Thermal Cycler Dice (registered trademark) Real Time System III (manufactured by Takara Bio Inc.) as a thermal cycler, and a Ct value was measured.

Example 6: Reverse Transcription Activity Evaluation Test of Bca, Aac and Taq Mutants—1

Evaluation test 1 was performed using the Bca, Aac and Taq DNA polymerase mutants obtained in (3), (4) and (5) by the method described in Experimental method (6). Results are shown in Table 5. Each DNA polymerase mutant b13b46 comprised mutations corresponding to the mutations "Q682R+E689R" of Tth DNA polymerase mutant b13b46 (in other words, amino acids at positions corresponding to positions 682 and 689 in the amino acid sequence of Tth DNA polymerase were replaced by arginine).

TABLE 5

| Mutation type | Pol activity (U/µg) | Reverse transcription activity (U/µg) | RT\Pol activity ratio |
|---|---|---|---|
| Bca native-type | 127.9 | 25.5 | 1 |
| Bca mutant (b13b46) | 194.6 | 79.4 | 2 |
| Aac native-type | 73.9 | 8.5 | 1 |
| Aac mutant (b13b46) | 88.8 | 38.8 | 4 |
| Taq native-type | 82.26 | 1.1 | 1 |
| Taq mutant (b13b46) | 82.01 | 9.5 | 9 |

As shown in Table 5, the Bca (b13b46) mutant prepared in contrast to the Bca native-type had an enhanced reverse transcription activity while maintaining the polymerase The reverse transcription activity of the Bca activity. (b13b46) mutant was enhanced by about 2 times as compared to the native-type. In the case of Aac, the reverse transcription activity of the Aac (b13b46) mutant was enhanced by about 4 times as compared to the native-type while the polymerase activity was maintained. In the case of Taq, the reverse transcription activity of the Taq (b13b46) mutant was enhanced by about 9 times as compared to the native-type while the polymerase activity was maintained.

Example 7: Reverse Transcription Activity Evaluation Test of Bca, Aac and Taq Mutants—2

The amounts of cDNAs synthesized using the Bca, Aac and Taq DNA polymerase mutants obtained in (3), (4) and (5) were confirmed to evaluate the reverse transcription activity.

Evaluation test 2 was performed by the method described in Experimental method (7). Results are shown in Table 6.

TABLE 6

| | RT-PCR Ct value | |
|---|---|---|
| Mutation type | ΔCt | Conversion to starting amount of DNA template in PCR |
| Bca native-type | Standard value, (0) | 1 |
| Bca mutant (b13b46) | −10.18 | 1160 |
| Aac native-type | Standard value, (0) | 1 |
| Aac mutant (b13b46) | −9.35 | 653 |
| Taq native-type | Standard value, (0) | 1 |
| Taq mutant (b13b46) | −9.02 | 519 |

As shown in Table 6, the starting DNA template amount in PCR when each mutant was used was 510 to 1000 or more times that when the wild-type enzyme was used. The increase in the DNA template amount means that the amount of cDNA produced by reverse transcription reaction before PCR increased. Thus, it was found that the mutants had a 510 to 1000 or more times higher activity in the reverse transcription reaction than the wild-type enzymes. It was also found that the reverse transcriptase activity of DNA polymerases classified into Pol I type or Family A type can be improved according to the present invention.

INDUSTRIAL APPLICABILITY

According to the present invention, a DNA polymerase having a reverse transcriptase activity which is suitable for performing a reverse transcription reaction and a nucleic acid amplification reaction in the same container is provided. Use of the DNA polymerase enables an efficient reverse transcription reaction even when an RNA having rigid secondary structure, which has been difficult to be reverse transcribed, is used as a template. Further, the increased efficiency of reverse transcription reaction enables detection in a shorter time and with similar or higher sensitivity than conventional enzymes when a reverse transcription reaction and a nucleic acid amplification reaction are continuously performed in the same container. Thus, the DNA polymerase having a reverse transcriptase activity of the present invention is useful in a wide range of fields including genetic engineering, biology, medical science, and agriculture.

Sequence Listing Free Text
SEQ ID NO: 1: DNA polymerase I *Thermus thermophilus*
SEQ ID NO: 2: PCR forward Primer lambda RNA
SEQ ID NO: 3: PCR Reverse Primer lambda RNA
SEQ ID NO: 4: Probe lambda RNA. 5'-end is labeled FAM and 3'-end is labeled BHQ1
SEQ ID NO: 5: DNA polymerase variant Tth b13
SEQ ID NO: 6: DNA polymerase variant Tth b13
SEQ ID NO: 7: DNA polymerase variant Tth b46
SEQ ID NO: 8: DNA polymerase variant Tth b46
SEQ ID NO: 9: DNA polymerase variant Tth b13 b46
SEQ ID NO: 10: DNA polymerase variant Tth b13 b46
SEQ ID NO: 11: PIP-L14-PIP-L14-PIP-L15 Tth
SEQ ID NO: 12: PCR forward Primer COG1F
SEQ ID NO: 13: PCR Reverse Primer COG1R
SEQ ID NO: 14: PCR forward Primer COG2F
SEQ ID NO: 15: PCR Reverse Primer COG2R
SEQ ID NO: 16: Probe RING1-TP (a). 5'-end is labeled Cy5 and 3'-end is labeled BHQ3
SEQ ID NO: 17: Probe RING2AL-TP. 5'-end is labeled ROX and 3'-end is labeled BHQ2
SEQ ID NO: 18: A partial sequence (A1-A12) of Tth DNA polymerase
SEQ ID NO: 19: A partial sequence (A1-A12) of Tth DNA polymerase variant
SEQ ID NO: 20: A partial sequence (A1-A12) of Bca polymerase
SEQ ID NO: 21: A partial sequence (A1-A12) of Bst polymerase
SEQ ID NO: 22: A partial sequence (A1-A12) of Aac polymerase
SEQ ID NO: 23: DNA polymerase I *Bacillus* caldotenax
SEQ ID NO: 24: DNA polymerase I *Alicyclobacillus acidocaldarius*
SEQ ID NO: 25: DNA polymerase I *Thermus aquaticus*
SEQ ID NO: 26: PCR forward Primer hACTB-F
SEQ ID NO: 27: PCR Reverse Primer hACTB-533
SEQ ID NO: 28: DNA polymerase I *Bacillus stearothermophilus*

The invention claimed is:

1. A mutant of a DNA polymerase derived from *Bacillus caldotenax*, the DNA polymerase having reverse transcriptase activity,
wherein the DNA polymerase is the amino acid sequence set forth in SEQ ID NO:23, and comprises a sequence consisting of 12 amino acids A1-A12 set forth in SEQ ID NO: 20;
wherein the mutant comprises a sequence consisting of the 12 amino acids A1-A12, except that either (i) A3 is replaced by a basic amino acid residue, (ii) A10 is replaced by arginine or histidine, or (iii) A3 is replaced by a basic amino acid residue and A10 is replaced by arginine or histidine,
wherein, in the portion outside the 12 amino acid sequence of A1-A12, the mutant has at least 90% amino acid sequence identity to the amino acid sequence set forth in SEQ ID NO: 23, and wherein the reverse transcriptase activity in the mutant is improved relative to the DNA polymerase.

2. The mutant according to claim 1, wherein A3 or A10 or both A3 and A10 in the sequence consisting of 12 amino acids are replaced by arginine.

3. The mutant according to claim 1, wherein, in the portion outside the 12 amino acid sequence of A1-A12, the mutant has at least 95% amino acid sequence identity to the amino acid sequence set forth in SEQ ID NO: 23.

4. A kit containing the mutant according to claim 1.

5. A composition comprising the mutant according to claim 1.

* * * * *